(12) United States Patent
Dobak, III

(10) Patent No.: US 7,951,183 B2
(45) Date of Patent: May 31, 2011

(54) MEDICAL PROCEDURE

(75) Inventor: John D. Dobak, III, La Jolla, CA (US)

(73) Assignee: Innercool Therapies, Inc., San Diego, CA (US)

( * ) Notice: Subject to any disclaimer, the term of this patent is extended or adjusted under 35 U.S.C. 154(b) by 466 days.

(21) Appl. No.: 12/152,160

(22) Filed: May 13, 2008

(65) Prior Publication Data

US 2008/0221651 A1    Sep. 11, 2008

Related U.S. Application Data

(60) Division of application No. 10/934,096, filed on Sep. 3, 2004, now Pat. No. 7,371,254, which is a continuation-in-part of application No. 10/714,070, filed on Nov. 14, 2003, now Pat. No. 7,651,518, and a continuation-in-part of application No. 10/008,999, filed on Dec. 7, 2001, now Pat. No. 6,786,218, said application No. 10/714,070 is a continuation of application No. 10/095,753, filed on Mar. 11, 2002, now Pat. No. 6,695,873, which is a division of application No. 09/757,124, filed on Jan. 8, 2001, now Pat. No. 6,540,771, which is a division of application No. 09/215,038, filed on Dec. 16, 1998, now Pat. No. 6,261,312, which is a continuation-in-part of application No. 09/103,342, filed on Jun. 23, 1998, now Pat. No. 6,096,068, which is a continuation-in-part of application No. 09/047,012, filed on Mar. 24, 1998, now Pat. No. 5,957,963, which is a continuation-in-part of application No. 09/012,287, filed on Jan. 23, 1998, now Pat. No. 6,051,019, said application No. 10/008,999 is a division of application No. 09/539,932, filed on Mar. 31, 2000, now Pat. No. 6,491,039, which is a continuation-in-part of application No. 09/306,866, filed on May 7, 1999, now Pat. No. 6,235,048, which is a division of application No. 09/012,287, filed on Jan. 23, 1998, now Pat. No. 6,051,019, said application No. 09/539,932 is a continuation-in-part of application No. 09/373,112, filed on Aug. 11, 1999, now Pat. No. 6,843,800, which is a continuation-in-part of application No. 09/292,532, filed on Apr. 15, 1999, now abandoned, which is a continuation-in-part of application No. 09/103,342, filed on Jun. 23, 1998, now Pat. No. 6,096,068, and a continuation-in-part of application No. 09/052,545, filed on Mar. 31, 1998, now Pat. No. 6,231,595, and a continuation-in-part of application No. 09/047,012, filed on Mar. 24, 1998, now Pat. No. 5,957,963, which is a continuation-in-part of application No. 09/012,287, filed on Jan. 23, 1998, now Pat. No. 6,051,019.

(51) Int. Cl.
  *A61F 7/12* (2006.01)
(52) U.S. Cl. .......................... 607/106; 607/104; 607/105
(58) Field of Classification Search .................... 607/96, 607/104–107
  See application file for complete search history.

(56) References Cited

U.S. PATENT DOCUMENTS

| | | | |
|---|---|---|---|
| 2,308,484 A | 1/1943 | Auzin et al. |
| 2,374,609 A | 4/1945 | McCollum |
| 2,615,686 A | 10/1952 | Davidson |
| 2,672,032 A | 3/1954 | Towse |
| 2,913,009 A | 11/1959 | Kuthe |
| 3,125,096 A | 3/1964 | Antiles et al. |
| 3,298,371 A | 1/1967 | Lee |
| 3,425,419 A | 2/1969 | Dato |
| 3,460,538 A | 8/1969 | Armstrong |
| 3,504,674 A | 4/1970 | Swenson et al. |
| 3,604,419 A | 9/1971 | Diskin et al. |
| 3,612,175 A | 10/1971 | Ford et al. |
| 3,674,031 A | 7/1972 | Weiche |
| 3,865,116 A | 2/1975 | Brooks |
| 3,888,259 A | 6/1975 | Miley |
| 3,971,383 A | 7/1976 | Van Gerven |
| 4,038,519 A | 7/1977 | Foucras |
| 4,153,048 A | 5/1979 | Magrini |
| 4,160,455 A | 7/1979 | Law |
| 4,190,033 A | 2/1980 | Foti |
| 4,216,767 A | 8/1980 | Aoshiro |

| | | | | | |
|---|---|---|---|---|---|
| 4,231,425 A | 11/1980 | Engstrom | 5,257,977 A | 11/1993 | Eshel |
| 4,241,729 A | 12/1980 | Aoshiro | 5,264,260 A | 11/1993 | Saab |
| 4,275,734 A | 6/1981 | Mitchiner | 5,267,341 A | 11/1993 | Shearin |
| 4,298,006 A | 11/1981 | Parks | 5,269,369 A | 12/1993 | Faghri |
| 4,318,722 A | 3/1982 | Altman | 5,269,749 A | 12/1993 | Koturov |
| 4,323,071 A | 4/1982 | Simpson et al. | 5,269,758 A | 12/1993 | Taheri |
| 4,427,009 A | 1/1984 | Wells et al. | 5,279,299 A | 1/1994 | Imran |
| 4,445,500 A | 5/1984 | Osterholm | 5,281,213 A | 1/1994 | Milder et al. |
| 4,464,172 A | 8/1984 | Lichtenstein | 5,281,215 A | 1/1994 | Milder |
| 4,483,341 A | 11/1984 | Witteles | 5,306,261 A | 4/1994 | Alliger et al. |
| 4,484,586 A | 11/1984 | McMickle et al. | 5,310,440 A | 5/1994 | Zingher |
| 4,502,286 A | 3/1985 | Okada et al. | 5,322,514 A | 6/1994 | Steube et al. |
| 4,569,355 A | 2/1986 | Bitterly | 5,322,515 A | 6/1994 | Karas et al. |
| 4,581,017 A | 4/1986 | Sahota | 5,322,518 A | 6/1994 | Schneider et al. |
| 4,602,642 A | 7/1986 | O'Hara et al. | 5,326,165 A | 7/1994 | Walthall et al. |
| 4,625,712 A | 12/1986 | Wampler ............... 128/1 D | 5,326,166 A | 7/1994 | Walthall et al. |
| 4,655,746 A | 4/1987 | Daniels et al. | 5,330,435 A | 7/1994 | Vaillancourt |
| 4,672,962 A | 6/1987 | Hershenson | 5,330,519 A | 7/1994 | Mason et al. |
| 4,731,072 A | 3/1988 | Aid | 5,334,193 A | 8/1994 | Nardella |
| 4,739,492 A | 4/1988 | Cochran | 5,342,301 A | 8/1994 | Saab |
| 4,745,922 A | 5/1988 | Taylor | 5,342,621 A | 8/1994 | Eury |
| 4,747,826 A | 5/1988 | Sassano | 5,344,436 A | 9/1994 | Fontenot et al. |
| 4,748,979 A | 6/1988 | Hershenson | 5,344,740 A | 9/1994 | Iwasawa et al. |
| 4,750,493 A | 6/1988 | Brader | 5,354,272 A | 10/1994 | Swendson et al. |
| 4,762,129 A | 8/1988 | Bonzel | 5,358,486 A | 10/1994 | Saab |
| 4,762,130 A | 8/1988 | Fogarty et al. | 5,364,364 A | 11/1994 | Kasvikis et al. |
| 4,781,799 A | 11/1988 | Herbert, Jr. et al. | 5,365,750 A | 11/1994 | Greenthal |
| 4,796,640 A | 1/1989 | Webler | 5,368,591 A | 11/1994 | Lennox et al. |
| 4,817,624 A | 4/1989 | Newbower | 5,383,854 A | 1/1995 | Safar et al. |
| 4,819,655 A | 4/1989 | Webler | 5,383,918 A | 1/1995 | Panetta |
| 4,820,349 A | 4/1989 | Saab | 5,395,314 A | 3/1995 | Klatz et al. |
| 4,837,228 A | 6/1989 | Elsohly et al. | 5,395,331 A | 3/1995 | O'Neill et al. |
| 4,860,744 A | 8/1989 | Johnson et al. | 5,403,281 A | 4/1995 | O'Neill et al. |
| 4,883,455 A | 11/1989 | Leonard | 5,417,686 A | 5/1995 | Peterson et al. |
| 4,894,164 A | 1/1990 | Polaschegg | 5,423,745 A | 6/1995 | Todd et al. |
| 4,904,237 A | 2/1990 | Janese | 5,423,807 A | 6/1995 | Milder |
| 4,920,963 A | 5/1990 | Brader | 5,433,740 A | 7/1995 | Yamaguchi |
| 4,951,677 A | 8/1990 | Crowlet et al. | 5,437,673 A | 8/1995 | Baust et al. |
| 4,964,409 A | 10/1990 | Tremulis | 5,443,456 A | 8/1995 | Alliger et al. |
| 4,969,470 A | 11/1990 | Mohl et al. | 5,462,521 A | 10/1995 | Brucker et al. |
| 4,973,493 A | 11/1990 | Guire | 5,486,204 A | 1/1996 | Clifton |
| 4,979,959 A | 12/1990 | Guire | 5,486,208 A | 1/1996 | Ginsburg |
| 5,000,734 A | 3/1991 | Boussignac et al. | 5,496,271 A | 3/1996 | Burton et al. |
| 5,002,531 A | 3/1991 | Bonzel | 5,496,311 A | 3/1996 | Abele et al. |
| 5,014,695 A | 5/1991 | Benak et al. | 5,499,973 A | 3/1996 | Saab |
| 5,018,521 A | 5/1991 | Campbell | 5,520,682 A | 5/1996 | Baust et al. |
| 5,019,075 A | 5/1991 | Spears et al. | 5,531,776 A | 7/1996 | Ward et al. |
| 5,024,668 A | 6/1991 | Peters et al. | 5,536,247 A | 7/1996 | Thornton |
| 5,041,089 A | 8/1991 | Mueller et al. | 5,536,251 A | 7/1996 | Evard et al. ............... 604/93 |
| 5,046,497 A | 9/1991 | Millar | 5,545,133 A | 8/1996 | Burns et al. |
| 5,059,057 A | 10/1991 | Graef | 5,545,708 A | 8/1996 | Onwunaka et al. |
| 5,078,713 A | 1/1992 | Varney | 5,549,559 A | 8/1996 | Eshel |
| 5,089,260 A | 2/1992 | Hunter et al. | 5,554,119 A | 9/1996 | Harrison et al. |
| 5,092,841 A | 3/1992 | Spears | 5,558,644 A | 9/1996 | Boyd et al. |
| 5,106,360 A | 4/1992 | Ishiwara et al. | 5,569,195 A | 10/1996 | Saab |
| 5,106,368 A | 4/1992 | Uldall et al. | 5,573,532 A | 11/1996 | Chang et al. |
| 5,108,390 A | 4/1992 | Potocky et al. | 5,578,008 A | 11/1996 | Hara |
| RE33,911 E | 5/1992 | Samson et al. | 5,584,804 A | 12/1996 | Klatz et al. |
| 5,110,721 A | 5/1992 | Anaise et al. | 5,588,438 A | 12/1996 | McKown et al. |
| 5,112,438 A | 5/1992 | Bowers | 5,591,162 A | 1/1997 | Fletcher et al. |
| 5,117,822 A | 6/1992 | Laghi | 5,617,854 A | 4/1997 | Munsif |
| 5,139,496 A | 8/1992 | Hed ............... 606/23 | 5,620,480 A | 4/1997 | Rudie |
| 5,147,355 A | 9/1992 | Friedman et al. | 5,622,182 A | 4/1997 | Jaffe |
| 5,149,321 A | 9/1992 | Klatz et al. | 5,624,342 A | 4/1997 | Younger |
| 5,150,706 A | 9/1992 | Cox et al. | 5,624,392 A | 4/1997 | Saab |
| 5,151,100 A | 9/1992 | Abele et al. | 5,630,837 A | 5/1997 | Crowley |
| 5,156,151 A | 10/1992 | Imran | 5,643,197 A | 7/1997 | Brucker et al. |
| 5,180,364 A | 1/1993 | Ginsburg | 5,647,051 A | 7/1997 | Neer |
| 5,190,539 A | 3/1993 | Fletcher et al. | 5,653,692 A | 8/1997 | Masterson et al. |
| 5,191,883 A | 3/1993 | Lennox et al. | 5,676,693 A | 10/1997 | Lafontaine |
| 5,196,024 A | 3/1993 | Barath | 5,709,654 A | 1/1998 | Klatz et al. |
| 5,211,631 A | 5/1993 | Sheaff | 5,713,941 A | 2/1998 | Robins et al. |
| 5,234,405 A | 8/1993 | Klatz et al. | 5,716,386 A | 2/1998 | Ward et al. |
| 5,236,908 A | 8/1993 | Gruber et al. | 5,733,318 A | 3/1998 | Augustine |
| 5,239,999 A | 8/1993 | Imran | 5,733,319 A | 3/1998 | Neilson et al. |
| 5,246,421 A | 9/1993 | Saab | 5,735,290 A | 4/1998 | Sterman et al. ............... 128/898 |
| 5,247,434 A | 9/1993 | Peterson et al. ............... 700/83 | 5,735,809 A | 4/1998 | Gorsuch |
| 5,248,312 A | 9/1993 | Langberg | 5,766,151 A | 6/1998 | Valley et al. ............... 604/96 |
| 5,250,070 A | 10/1993 | Parodi | 5,797,878 A | 8/1998 | Bleam |

| | | | | | |
|---|---|---|---|---|---|
| 5,799,661 A | 9/1998 | Boyd et al. | 6,238,428 B1 | 5/2001 | Werneth et al. |
| 5,800,480 A | 9/1998 | Augustine et al. | 6,245,095 B1 | 6/2001 | Dobak, III et al. |
| 5,800,483 A | 9/1998 | Vought | 6,251,093 B1 | 6/2001 | Valley et al. |
| 5,800,486 A | 9/1998 | Thome | 6,251,129 B1 | 6/2001 | Dobak, III et al. |
| 5,800,488 A | 9/1998 | Crockett | 6,251,130 B1 | 6/2001 | Dobak, III et al. |
| 5,800,493 A | 9/1998 | Stevens et al. | 6,253,769 B1 | 7/2001 | Lafontaine et al. |
| 5,800,516 A | 9/1998 | Fine et al. | 6,254,626 B1 | 7/2001 | Dobak, III et al. |
| 5,807,318 A | 9/1998 | St. Goar et al. ............... 604/53 | 6,261,312 B1 | 7/2001 | Dobak, III et al. |
| 5,807,391 A | 9/1998 | Wijkamp | 6,264,679 B1 | 7/2001 | Keller et al. |
| 5,820,593 A | 10/1998 | Safar et al. | 6,277,143 B1 | 8/2001 | Klatz et al. |
| 5,824,030 A | 10/1998 | Yang et al. | 6,287,326 B1 | 9/2001 | Pecor |
| 5,827,222 A | 10/1998 | Klatz et al. | 6,290,674 B1 | 9/2001 | Roue et al. |
| 5,827,237 A | 10/1998 | Macoviak et al. | 6,290,697 B1 | 9/2001 | Tu et al. |
| 5,827,269 A | 10/1998 | Saadat | 6,290,717 B1 | 9/2001 | Philips |
| 5,833,671 A | 11/1998 | Macoviak et al. | 6,295,990 B1 | 10/2001 | Lewis et al. |
| 5,833,673 A | 11/1998 | Ockuly et al. | 6,299,599 B1 | 10/2001 | Pham et al. |
| 5,834,465 A | 11/1998 | Olney | 6,306,161 B1 | 10/2001 | Ginsburg |
| 5,837,003 A | 11/1998 | Ginsburg | 6,312,452 B1 | 11/2001 | Dobak, III et al. |
| 5,855,210 A | 1/1999 | Sterman et al. ............... 128/898 | 6,315,754 B1 | 11/2001 | Daoud et al. |
| 5,861,021 A | 1/1999 | Thome et al. | 6,319,248 B1 | 11/2001 | Nahon |
| 5,868,735 A | 2/1999 | Lafontaine | 6,325,818 B1 | 12/2001 | Werneth |
| 5,871,468 A | 2/1999 | Kramer et al. | 6,336,911 B1 | 1/2002 | Westerbeck |
| 5,871,526 A | 2/1999 | Gibbs et al. | 6,338,727 B1 | 1/2002 | Noda et al. |
| 5,873,835 A | 2/1999 | Hastings et al. | 6,354,099 B1 | 3/2002 | Bieberich |
| 5,879,316 A | 3/1999 | Safar et al. | 6,364,899 B1 | 4/2002 | Dobak, III |
| 5,879,329 A | 3/1999 | Ginsburg | 6,365,338 B1 | 4/2002 | Bull et al. |
| 5,888,241 A | 3/1999 | Jarvik ............... 623/3 | 6,365,579 B2 | 4/2002 | Thatcher et al. |
| 5,891,094 A | 4/1999 | Masterson et al. | 6,368,304 B1 | 4/2002 | Aliberto et al. |
| 5,899,898 A | 5/1999 | Arless et al. | 6,379,378 B1 | 4/2002 | Werneth et al. |
| 5,899,899 A | 5/1999 | Arless et al. | 6,383,210 B1 | 5/2002 | Magers et al. |
| 5,902,268 A | 5/1999 | Saab | 6,393,320 B2 | 5/2002 | Lasersohn et al. |
| 5,906,588 A | 5/1999 | Safar et al. | 6,405,080 B1 | 6/2002 | Lasersohn et al. |
| 5,906,594 A | 5/1999 | Scarfone et al. | 6,409,747 B1 | 6/2002 | Gobin et al. |
| 5,906,636 A | 5/1999 | Casscells, III et al. | 6,416,533 B1 | 7/2002 | Gobin et al. |
| 5,910,104 A | 6/1999 | Dobak, III et al. | 6,419,643 B1 | 7/2002 | Shimada et al. |
| 5,913,856 A | 6/1999 | Chia et al. | 6,432,102 B2 | 8/2002 | Joye et al. |
| 5,913,876 A | 6/1999 | Taylor et al. ............... 607/2 | 6,432,124 B1 | 8/2002 | Worthen et al. |
| 5,913,885 A | 6/1999 | Klatz et al. | 6,436,130 B1 | 8/2002 | Philips et al. |
| 5,913,886 A | 6/1999 | Soloman | 6,436,131 B1 | 8/2002 | Ginsburg |
| 5,916,242 A | 6/1999 | Schwartz | 6,464,716 B1 | 10/2002 | Dobak, III et al. |
| 5,954,741 A | 9/1999 | Fox ............... 606/198 | 6,468,296 B1 | 10/2002 | Dobak, III et al. |
| 5,957,879 A | 9/1999 | Roberts et al. ............... 604/4 | 6,497,721 B2 | 12/2002 | Ginsburg et al. |
| 5,957,917 A | 9/1999 | Doiron et al. | 6,520,933 B1 | 2/2003 | Evans et al. |
| 5,957,963 A | 9/1999 | Dobak, III | 6,540,771 B2 | 4/2003 | Dobak, III |
| 5,964,751 A | 10/1999 | Amplatz et al. | 6,544,282 B1 | 4/2003 | Dae et al. ............... 607/105 |
| 5,967,976 A | 10/1999 | Larson et al. | 6,572,638 B1 | 6/2003 | Dae et al. |
| 5,968,009 A | 10/1999 | Siman | 6,572,640 B1 | 6/2003 | Balding et al. |
| 5,971,979 A | 10/1999 | Joye et al. | 6,602,276 B2 | 8/2003 | Dobak, III et al. |
| 5,989,238 A | 11/1999 | Ginsburg | 6,641,603 B2 | 11/2003 | Walker et al. |
| 6,006,134 A | 12/1999 | Hill et al. ............... 607/9 | 6,648,908 B2 | 11/2003 | Dobak, III |
| 6,007,692 A | 12/1999 | Herbert et al. | 2001/0001830 A1 | 5/2001 | Dobak, III et al. |
| 6,011,995 A | 1/2000 | Guglielmi et al. | 2001/0001831 A1 | 5/2001 | Dobak, III et al. |
| 6,015,378 A | 1/2000 | Borst et al. ............... 600/37 | 2001/0001832 A1 | 5/2001 | Dobak, III et al. |
| 6,019,783 A | 2/2000 | Philips et al. | 2001/0002442 A1 | 5/2001 | Dobak, III |
| 6,022,336 A | 2/2000 | Zadno-Azizi et al. | 2001/0005791 A1 | 6/2001 | Ginsburg et al. |
| 6,024,740 A | 2/2000 | Lesh et al. | 2001/0007951 A1 | 7/2001 | Dobak, III |
| 6,033,383 A | 3/2000 | Ginsburg | 2001/0008975 A1 | 7/2001 | Dobak, III et al. |
| 6,042,559 A | 3/2000 | Dobak, III | 2001/0010011 A1 | 7/2001 | Aliberto et al. |
| 6,051,019 A | 4/2000 | Dobak, III | 2001/0011146 A1 | 8/2001 | Joh et al. |
| 6,063,101 A | 5/2000 | Jacobsen et al. | 2001/0011184 A1 | 8/2001 | Dobak, III et al. |
| 6,096,068 A | 8/2000 | Dobak, III et al. | 2001/0011185 A1 | 8/2001 | Dobak, III et al. |
| 6,110,168 A | 8/2000 | Ginsburg | 2001/0014799 A1 | 8/2001 | Schwartz |
| 6,126,684 A | 10/2000 | Gobin et al. | 2001/0014802 A1 | 8/2001 | Tu |
| 6,146,411 A | 11/2000 | Noda et al. | 2001/0016763 A1 | 8/2001 | Lasheras et al. |
| 6,146,814 A | 11/2000 | Millet | 2001/0016764 A1 | 8/2001 | Dobak, III |
| 6,149,670 A | 11/2000 | Worthen et al. | 2001/0021865 A1 | 9/2001 | Dobak, III et al. |
| 6,149,673 A | 11/2000 | Ginsburg | 2001/0021866 A1 | 9/2001 | Dobak, III et al. |
| 6,149,676 A | 11/2000 | Ginsburg | 2001/0027333 A1 | 10/2001 | Schwartz |
| 6,149,677 A | 11/2000 | Dobak, III | 2001/0029394 A1 | 10/2001 | Dobak, III et al. |
| 6,165,207 A | 12/2000 | Balding et al. | 2001/0031946 A1 | 10/2001 | Walker et al. |
| 6,190,354 B1 | 2/2001 | LaFontaine et al. | 2001/0032003 A1 | 10/2001 | Pecor |
| 6,194,899 B1 | 2/2001 | Ishihara et al. | 2001/0032004 A1 | 10/2001 | Werneth |
| 6,200,280 B1 | 3/2001 | Brenneman et al. | 2001/0039440 A1 | 11/2001 | Lasheras et al. |
| 6,206,004 B1 | 3/2001 | Schmidt et al. | 2001/0041923 A1 | 11/2001 | Dobak, III |
| 6,224,624 B1 | 5/2001 | Lasheras et al. | 2001/0044644 A1 | 11/2001 | Keller et al. |
| 6,230,501 B1 | 5/2001 | Bailey et al. ............... 62/51.1 | 2001/0047191 A1 | 11/2001 | Lasersohn et al. |
| 6,231,594 B1 | 5/2001 | Dae | 2001/0047192 A1 | 11/2001 | Lasersohn et al. |
| 6,231,595 B1 | 5/2001 | Dobak, III | 2001/0047196 A1 | 11/2001 | Ginsburg |
| 6,235,048 B1 | 5/2001 | Dobak, III | 2001/0049545 A1 | 12/2001 | Lasersohn et al. |

| | | | |
|---|---|---|---|
| 2002/0002394 A1 | 1/2002 | Dobak, III | |
| 2002/0004675 A1 | 1/2002 | Lasheras | |
| 2002/0007179 A1 | 1/2002 | Dobak, III et al. | |
| 2002/0007202 A1 | 1/2002 | Dobak, III et al. | |
| 2002/0007203 A1 | 1/2002 | Gilmartin et al. | |
| 2002/0016621 A1 | 2/2002 | Werneth et al. | |
| 2002/0022823 A1 | 2/2002 | Luo et al. | |
| 2002/0026227 A1 | 2/2002 | Phillips | |
| 2002/0029016 A1 | 3/2002 | Pham et al. | |
| 2002/0032430 A1 | 3/2002 | Luo et al. | |
| 2002/0032474 A1 | 3/2002 | Dobak, III et al. | |
| 2002/0040717 A1 | 4/2002 | Dobak, III | |
| 2002/0045892 A1 | 4/2002 | Kramer | |
| 2002/0045925 A1 | 4/2002 | Keller et al. | |
| 2002/0049409 A1 | 4/2002 | Noda et al. | |
| 2002/0049410 A1 | 4/2002 | Noda et al. | |
| 2002/0049484 A1 | 4/2002 | Werneth et al. | |
| 2002/0056281 A1 | 5/2002 | Bieberich | |
| 2002/0066458 A1 | 6/2002 | Aliberto et al. | |
| 2002/0068964 A1 | 6/2002 | Dobak, III | |
| 2002/0077665 A1 | 6/2002 | Kordis et al. | |
| 2002/0077680 A1 | 6/2002 | Noda | |
| 2002/0082671 A1 | 6/2002 | Magers et al. | |
| 2002/0091378 A1 | 7/2002 | Dobak, III et al. | |
| 2002/0091429 A1 | 7/2002 | Dobak, III et al. | |
| 2002/0091430 A1 | 7/2002 | Dobak, III et al. | |
| 2002/0095200 A1 | 7/2002 | Dobak, III et al. | |
| 2002/0095201 A1 | 7/2002 | Worthen et al. | |
| 2002/0099427 A1 | 7/2002 | Dobak, III | |
| 2002/0103519 A1 | 8/2002 | Dobak, III et al. | |
| 2002/0111616 A1 | 8/2002 | Dae et al. | |
| 2002/0111657 A1 | 8/2002 | Dae et al. | |
| 2002/0138121 A1 | 9/2002 | Fox | |
| 2002/0151945 A1 | 10/2002 | Gobin et al. | |
| 2002/0151946 A1 | 10/2002 | Dobak, III | |
| 2002/0156421 A1 | 10/2002 | Noda et al. | |
| 2002/0161331 A1 | 10/2002 | Noda et al. | |
| 2002/0169490 A1 | 11/2002 | Noda et al. | |
| 2002/0193853 A1 | 12/2002 | Worthen et al. | |
| 2003/0014094 A1 | 1/2003 | Hammack et al. | |
| 2003/0028212 A1 | 2/2003 | Saab | |
| 2003/0040782 A1 | 2/2003 | Walker et al. | |
| 2003/0092975 A1 | 5/2003 | Casscells et al. | |
| 2004/0050154 A1 | 3/2004 | Machold et al. | |
| 2004/0147914 A1 | 7/2004 | Kramer | |

FOREIGN PATENT DOCUMENTS

| | | |
|---|---|---|
| AU | 730835 B2 | 3/2001 |
| AU | 734506 B2 | 6/2001 |
| AU | 739996 B2 | 2/2002 |
| AU | 743945 B2 | 2/2002 |
| EP | 0655225 A1 | 5/1993 |
| EP | 0664990 | 11/1997 |
| EP | 0428505 B2 | 3/2001 |
| EP | 1172932 A2 | 7/2001 |
| EP | 1205167 A2 | 5/2002 |
| FR | 2 447 406 | 3/1980 |
| SU | 806 029 | 2/1981 |
| WO | WO 91/05528 | 5/1991 |
| WO | WO 93/04727 | 3/1993 |
| WO | WO 95/01814 | 1/1995 |
| WO | WO 96/40347 | 12/1996 |
| WO | WO 97/01374 | 1/1997 |
| WO | WO 97/25011 | 7/1997 |
| WO | WO 97/32518 | 9/1997 |
| WO | WO 98/26831 | 6/1998 |
| WO | WO 98/31312 | 7/1998 |
| WO | WO 98/38934 | 9/1998 |
| WO | WO 98/49957 | 11/1998 |
| WO | WO 99/02096 | 1/1999 |
| WO | WO 99/04211 | 1/1999 |
| WO | WO 99/37226 | 7/1999 |
| WO | WO 99/44519 | 9/1999 |
| WO | WO 99/48449 | 9/1999 |
| WO | WO 99/56812 | 11/1999 |
| WO | WO 99/66970 | 12/1999 |
| WO | WO 99/66971 | 12/1999 |
| WO | WO 00/09054 | 2/2000 |
| WO | WO 00/47145 | 2/2000 |
| WO | WO 00/10494 | 3/2000 |
| WO | WO 00/38601 | 7/2000 |
| WO | WO 00/48670 | 8/2000 |
| WO | WO 00/51534 | 9/2000 |
| WO | WO 00/53135 | 9/2000 |
| WO | WO 00/57823 | 10/2000 |
| WO | WO 00/57834 | 10/2000 |
| WO | WO 00/62837 | 10/2000 |
| WO | WO 00/66053 | 11/2000 |
| WO | WO 00/72779 | 12/2000 |
| WO | WO 00/72787 | 12/2000 |
| WO | WO 01/03606 | 1/2001 |
| WO | WO 01/08580 | 2/2001 |
| WO | WO 01/10323 | 2/2001 |
| WO | WO 01/10365 | 2/2001 |
| WO | WO 01/12061 | 2/2001 |
| WO | WO 01/12122 | 2/2001 |
| WO | WO 01/13809 | 3/2001 |
| WO | WO 01/13837 | 3/2001 |
| WO | WO 01/17471 | 3/2001 |
| WO | WO 01/19447 | 3/2001 |
| WO | WO 01/23035 | 4/2001 |
| WO | WO 01/26590 | 4/2001 |
| WO | WO 01/30413 | 5/2001 |
| WO | WO 01/41695 | 6/2001 |
| WO | WO 01/41708 | 6/2001 |
| WO | WO 01/43661 | 6/2001 |
| WO | WO 01/49236 | 7/2001 |
| WO | WO 01/50987 | 7/2001 |
| WO | WO 01/52781 | 7/2001 |
| WO | WO 01/56517 | 8/2001 |
| WO | WO 01/58397 | 8/2001 |
| WO | WO 01/64145 | 9/2001 |
| WO | WO 01/64146 | 9/2001 |
| WO | WO 01/66052 | 9/2001 |
| WO | WO 01/74276 | 10/2001 |
| WO | WO 01/76655 | 10/2001 |
| WO | WO 01/78580 | 10/2001 |
| WO | WO 01/87379 | 11/2001 |
| WO | WO 01/95840 | 12/2001 |
| WO | WO 02/07793 | 1/2002 |
| WO | WO 02/26175 | 4/2002 |
| WO | WO 02/26176 | 4/2002 |
| WO | WO 02/26285 | 4/2002 |
| WO | WO 02/26307 | 4/2002 |
| WO | WO 02/28300 | 4/2002 |
| WO | WO 02/36180 | 5/2002 |
| WO | WO 02/38091 | 5/2002 |
| WO | WO 02/43577 | 6/2002 |
| WO | WO 02/47577 | 6/2002 |
| WO | WO 02/47742 | 6/2002 |
| WO | WO 02/055129 | 7/2002 |

OTHER PUBLICATIONS

Ambrus; *The Biphasic Nature and Temperature Dependence of the Activation of Human Plaminogen by Urokinase*; May 1979; pp. 339-347; Research Communications in Chemical Pathology and Pharmacology, vol. 24, No. 2.

Bigelo; *Hypothermia, Its Possible Role in Cardiac Surgery*; Nov. 1959; pp. 849-866; Annals of Surgery, vol. 132, No. 5.

Cheatle; *Cryostripping the Long and Short Saphenous Veins*; Jan. 1993; one page; Br. J. Surg., vol. 80.

Dexter; *Blood Warms as It Blows Retrograde from a Femoral Cannulation Site to the Carotid Artery During Cardiopulmonary Bypass*; Nov. 1994; pp. 393-397; Perfusion, vol. 9, No. 6.

Gillinov; *Superior Cerebral Protection with Profound Hypothermia During Circulatory Arrest*; Nov. 1992; pp. 1432-1439; Ann. Thorac. Surg., vol. 55.

Higazi; *The Effect of Ultrasonic Irradiation and Temperature on Fibrinolytic Activity in Vitro*; Aug. 1992; p. 251-253; Thrombosis Research, vol. 69, No. 2.

Imamaki; *Retrograde Cerebral Perfusion with Hypothermic Blood Provides Efficient Protection of the Brain*; Jul. 1995; pp. 325-333; Journal of Cardiac Surgery, vol. 10, No. 4, Part 1.

Jolin; *Management of a Giant Intracranial Aneurysm Using Surface-Heparinized Extracorporeal Circulation and Controlled Deep Hypothermic Low Flow Perfusion*; Aug. 1992; pp. 756-760; Acta Anaesthesiologica Scandinavia.

Jos R.C. Jansen, Ph.D., et al. (1997) *Near Continuous Cardiac Output b Thermodilution*. Journal of Clinical Monitoring 13:233-239.

Kimoto; *Open Heart Surgery under Direct Vision with the Aid of Brain-Cooling by Irrigation*; Jul. 1955; pp. 592-603; Surgery, vol. 39, No. 4.

Marekovic, Z.; *Abstract of Renal Hypothermia in Situ by Venous Passages: Experimental Work on Dogs*; 1980; Eur Urol 6(2); 1 page.

Meden; *Effect of Hypothermia and Delayed Thrombolysis in a Rat Embolic Stroke Model*; Dec. 1993; pp. 91-98; Acta Neurologica Scandinavica.

Meden; *The Influence of Body Temperature on Infarct Volume and Thrombolytic Therapy in a Rat Embolic Stroke Model*; Feb. 1994; pp. 131-138; Brain Research, vol. 647.

Milleret, Rene; *La cryo-chirurgie danes les varices des mimbres inferieurs*; Angiologie; Supplement au No. 110.

Milleret; Abstract of *Cryosclerosis of the Saphenous Veins in Varicose Reflux in the Obese and Elderly*; Oct. 1981; one page; Phlebologie, vol. 34, No. 4.

Parkins; *Brain Cooling in the Prevention of Brain Damage During Periods of Circulatory Occlusion in Dogs*; Apr. 1954; pp. 284-289; Annals of Surgery, vol. 140, No. 3.

Piepgras; *Rapid Active Internal Core Cooling for Induction of Moderate Hypothermia in Head Injury by Use of an Extracorporeal Heat Exchanger*; Feb. 1998; pp. 311-318; Neurosurgery, vol. 42, No. 2.

Rijken; *Plasminogen Activation at Low Temperatures in Plasma Samples Containing Therapeutic Concentrations of Tissue-Type Plasminogen Activator or Other Thrombolytic Agents*; Oct. 1989; pp. 47-52; place of publication unknown.

Schwartz, A.E. et al.; (1996); *Isolated cerebral hypothermia by single carotid artery perfusion of extracorporeally cooled blood in baboons*; Neurosurgery 39(3):577-582.

Schwartz; *Cerebral Blood Flow during Low-flow Hypothermic Cardiopulmonary Bypass in Baboons*; Jun. 1994; pp. 959-964; Anesthesiology, vol. 81, No. 4.

Schwartz; *Selective Cerebral Hypothermia by Means of Transfemoral Internal Carotid Artery Catheterization*; May 1996; pp. 571-572; Radiology, vol. 201, No. 2.

Steen; *The Detrimental Effects of Prolonged Hypothermia and Rewarming in the Dog*; Aug. 1979; pp. 224-230; Anesthesiology, vol. 52, No. 3.

Vandam; *Hypothermia*; Sep. 1959; pp. 546-553; The New England Journal of Medicine.

White; *Cerebral Hypothermia and Circulatory Arrest*; Jul. 1978; pp. 450-458; Mayo Clinic Proceedings, vol. 53.

Yenari; *Thrombolysis with Tissue Plasminogen Activator (TPA) is Temperature Dependent*; Jul. 1994; pp. 475-481; Thrombosis Research, vol. 77, No. 5.

Yoshihara; *Changes in Coagulation and Fibrinolysis Occurring in Dogs during Hypothermia*; Aug. 1984; pp. 503-512; Thrombosis Research, vol. 37, No. 4.

Zarins; *Circulation in Profound Hypothermia*; Nov. 1972; pp. 97-104; Journal of Surgical Research, vol. 14, N. 2.

Colvett, K. T. et al. "Opportunities with Combined Modality Therapy for Selective Organ Preservation in Muscle-Invasive Bladder Cancer," May 1996, *Journ. Surg. Oncology* 63:202-201.

Mass, C. et al. "Intermittent Antegrade/Selective Cerebral Perfusion during Circulatory Arrest for Repair of the Aortic Arch," 1997, *Perfusion*, 12:127-132.

Alfonsi, P., D. I. Sessler, B. Du Manoir, J-C. Levron, J-P. Le Moing, M. Chauvin, *The Effects of Meperidine and Sufentanil on the Shivering Threshold in Postoperative Patients*, Anesthesiology, Jul. 1998, 89(1):43-48.

Anon, "Automatic feedback instrumentation for hospital room utilizing microsensors," *IBM Technical Disclosure Bulletin (ABS.)*, 29(3): 1 page, Aug. 1986.

Benzinger, T.H.; *On Physical Heart Regulation and Sense of Temperature in Man*; Naval Medical Research Institute; Physiology; vol. 45; pp. 645-659; (Feb. 26, 1959).

Brengelmann, George L.; *Specialized Brain Cooling in Humans?*; The FASEB Journal; vol. 7; pp. 1148-1153 (Sep. 1993).

Buggy, D., P. Higgins, C. Moran, F. O'Donovan, and M. McCarroll, *Clonidine at Induction Reduces Shivering after General Anaesthesia*, 1997, pp. 263-267, Can. J. Anaesth., vol. 44, N. 3.

Cabanac, M., *Selective Brain Cooling and Thermoregulatory Set-Point*, 1998, pp. 3-13, Journ. of Basic & Clinical Physiology & Pharmacology, vol. 9, N. 1.

Cabanac, M.; *Selective Brain Cooling in Humans: fancy or fact?*; The FASEB Journal; vol. 7; pp. 1143-1147 (Sep. 1993).

Capogna, G. and D. Celleno, *I. V. Clonidine for Post-Extradural Shivering in Parturients: A Preliminary Study*, 1993, Brit. Journ. of Anaesth., vol. 71.

Carrol et al. "A comparison of measurements from a temporal artery thermometer and a pulmonary artery thermistor—preliminary results." Fax Correspondence dated Oct. 19, 2001.

Cheng, C., T. Matsukawa, D. I. Sessler, M. Ozaki, A. Kurz, B. Merrifield, L. Hank, and P. Olofsson, *Increasing Mean Skin Temperature Linearly Reduces the Core-Temperature Thresholds for Vasoconstriction and Shivering in Humans*, May 1995, pp. 1160-1168, Anesthesiology, vol. 82, N. 5.

De Ford et al. "Design and evaluation of closed-loop feedback control of minimum temperatures in human intracranial tumours treated with interstitial hyperthermia," Med. & Biol. Eng. & Comput. 29:197-206, Mark 1991.

Deklunder, G., M. Dauzat, J-L. Lecroart, J-J. Hauser, and Y. Houdas, "Influence of Ventilation of the Face on Thermoregulation in Man during Hyper- and Hypothermia," *Eur. J. Appl. Physiol.*, 1991, 62:342-348.

Gentilello, L. M., "Advances in the Management of Hypothermia," *Horizons in Trauma Surgery*, 75(2):243-256, Apr. 1995.

Giesbrecht, G. G., M. S.. L. Goheen, C. E. Johnston, G. P. Kenny, G. K. Bristow, and J. S. Hayward, *Inhibition of Shivering Increases Core Temperature Afterdrop and Attenuates Rewarming in Hypothermic Humans*, 1997, 0161-7567:1630-1634, The American Physiological Society.

Giuffre, M., J. Finnie, D. A. Lynam, and D. Smith, *Rewarming Postoperative Patients: Lights, Blankets, or Forced Warm Air*, Dec. 1991, pp. 387-393, Journ. of Post Anaesthesia Nursing, vol. 6, N. 6.

Guffin, A., D. Girard, and J. A. Kaplan, *Shivering Following Cardiac Surgery: Hemodynamic Changes and Reversal*, Feb. 1987, pp. 24-28, Journ. of Cardiothoracic Anesthesia, vol. 1, N. 1.

Haley, E. C. et al. "A Randomized Trial of Tirilazad Mesylate in Patients with Acute Stroke (RANTTAS)," *Stroke*, 27(9):1453-1458, 1996.

Iaizzo, *Facial Warming Increases the Threshold for Shivering*, 1999; pp. 231-239, Journ. of Neurosurgical Anesthesiology, vol. 11, No. 4.

Keegan, M. T. et al. *Shivering Complicating the Treatment of Neurologically Impaired Surgical and Intensive Care Unit Patients*, Anesthesiology, 91(3):874-876, Sep. 1999.

Kogaku "Sensor technology to control artificial organs," KLA, 22(4):295-300, Aug. 1984 (in Japanese).

Kurz, Martin, et al.; "Naloxone, Meperidine, and Shivering."; *Anesthesiology*; 79 (6):1193-1201; Dec. 1993.

Lennon, R. L., M. P. Hosking, M. A. Conover, and W. J. Perkins, *Evaluation of a Forced-Air System for Warming Hypothermic Postoperative Patients*, 1990, pp. 424-427, Anesth. Analg., vol. 70.

Leslie, K., D. I. Sessler, A. R. Bjorksten, M. Ozaki, T. Matsukawa, and M. Schroeder, *Propofol Causes a Dose-Dependent Decrease in the Thermoregulatory Threshold for vasoconstriction but has Little Effect on Sweating*, Aug. 1994, pp. 353-360, vol. 81, N. 2.

Matsukawa, T., A. Kurz, D. I. Sessler, A. R. Bjorksten, B. Merrifield, and C. Cheng, *Propofol Linearly Reduces the Vasoconstriction and Shivering Thresholds*; May 1995, pp. 1169-1180, Anesthesiology, vol. 82, N. 5.

Möller et al. "Temperature control and light penetration in a feedback interstitial laser thermotherapy system," *Int. J. Hyperthermia*, 12(1):49-63, 1996.

Olshausen et al. "An isothermal flowmeter with improved frequency response for measuring tissue blood flow," Pflügers Arch, 367:97-102, 1976.

Pais, S. O., K. D. Tobin, C. B. Austin, and L. Queral, *Percutaneous Insertion of the Greenfield Inferior Vena Cava Filter: Experience with Ninety-Six Patients*, Oct. 1988, pp. 460-464, Journ. of Vascular Surg., vol. 8, N. 4.

Patton, J. H, T. C. Fabian, M. A. Croce, G. Minard, F. E. Pritchard, and K. A. Kudsk, *Prophylactic Greenfield Filters: Acute Complications*

*and Long-Term Follow-Up*, Aug. 1996; pp. 231-237; Journ. of Trauma: Injury, Infection, and Critical Care, vol. 41, N. 2.

Rohrer, M. J. and A. M. Natale, *Effect of Hypothermia on the Coagulation Cascade*, Oct. 1992, pp. 1402-1405, Critical Care Medicine, vol. 20, N. 10.

Schmid-Elsaesser, R. et al. (1999), *Combination Drug Therapy and Mild Hypothermia: A Promising Treatment Strategy for Reversible, Focal Cerebral Ischemia*, Stroke, 1891-1899, June.

Sessler, Daniel I.; "Mild Perioperative Hypothermia"; The New England Journal of Medicine; 336:1730-4737; Jun. 12, 1997.

Sharkey, A., J. M. Lipton, M. T. Murphy, and A. H. Giesecke, *Inhibition of Postanesthestic Shivering with Radiant Heat*, Feb. 1987, pp. 249-252, Anesthesiology, vol. 66, N. 2.

Shiraki, K., N. Konda, and S. Sagawa, Esphageal and Tympanic Temperature Responses to Core Blood Temperature Changes during Hyperthermia, *J. Appl. Physiol.* 61(1): 98-102 (1986).

Simon, M., C. A. Athanasoulis, D. Kim, F. L. Steinberg, D. H Porter, B. H. Byse, S. Kleshinski, S. Geller, D. E. Orron, and A. C. Waltman; *Simon Nitinol Inferior Vena Cava Filter: Initial Clinical Experience*, Jul. 1989, pp. 99-103; Radiology.

Villamaria, F. J., C. E. Baisden, A. Hillis, M. H. Rajab, and P. A. Rinaldi, "Forced-Air Warming is No More Effective than Conventional Methods for Raising Postoperative Core Temperature After Cardiac Surgery," *Journ. Cardiothoracic and Vascular Anesth.*,11(6):708-711, Oct. 1997.

Zweifler, R. M. and D. I. Sessler, "Thermoregulatory Vasoconstriction and Shivering Impede Therapeutic Hypothermia in Acute Ischemic Stroke Patients," *Journ. Stroke and Cerebrovascular Diseases*, 6(2):100-104, 1996.

Schwartz, Arthur E., et al.; Isolated Cerebral Hypothermia by Single Carotid Artery Perfusion of Extracorporeally Cooled Blood in Baboons; Neurosurgery, vol. 39, No. 3, pp. 577-582 (Sep. 1996).

Acton, J. C., L. C. Sheppard, N. T. Kouchoukos, J. W. Kirklin, *Automated Care System for Critically Ill Patients Following Cardiac Surgery*, Dept. of Surgery, University of Alabama in Birmingham, Birmingham, Alabama 35294, pp. 111-115.

Felberg, R. A., D. E. Krieger, R. Chuang, D. E. Persse, W. S. Burgin, S. L. Hickenbottom, L. B. Morgenstern, O. Rosales, and J. C. Grotta, "Hypothermia After Cardiac Arrest: Fesibility and Safety of an External Cooling Protocol," *Circulation*, Oct. 9, 2001, 1799-1804.

Rao, S. K., R. W. Schultz, H. Feinberg, and S. Levitsky, "Metabolic Evidence that Regional Hypothermia Induced by Cold Saline Protects the Heart during Ischemic Arrest," *Journ. of Surg. Res.* 20:421-425 (1976).

Kirkpatrick, W. G. et al. "Frequency of Complications with Prolonged Femoral Vein Catheterization for Hemodialysis Access," *Nephron* 1995, 73:58-62.

Kurz, A. et al. "Perioperative Normothermia to Reduce the Incidence of surgical-Wound Infection and Shorten Hospitalization," *The New England Journ. of Medicine*, May 9, 1996, 334(19):1209-1215.

Kvilekval, K. H. V. et al. "Complications of Percutaneous Intra-Aortic Balloon Pump Use in Patients with Peripheral Vascular Disease," *Arch. Surg.*, May 1991, 126:621-623.

Leslie, K. et al. "The Implications of Hypothermia for Early tracheal extubation Following Cardiac Surgery," *Journ. of Cardiothoracic and Vascular Anesth.* Dec. 1998, 12:6:30-34.

Levy, J. M. and S. J. Hessel, "Complications of Angiography and Interventional Radiology," *The Abdomen and the Pelvis*, Chap. 42, 1024-1051.

Mackenzie, D. J. et al. "Vascular Complications of the Intra-aortic Balloon Pump," *The American Journal of Surgery*, Nov. 1992, 164:517-521.

Makhoul, R. G. et al. "Vascular Complications of the Intra-aortic Balloon Pump: An Analysis of 436 Patients," *The American Surgeon*, Sep. 1993, 59:564-568.

Mian, N. Z. et al. "Incidence of Deep Venous Thrombosis Associated with Femoral Venous Catheterization,"*Acad. Emergency Medicine*, Dec. 1997,4(12):1118-1121.

Miller, J. S. et al. "Vascular Complications Following Intra-Aortic Balloon Pump Insertion," *The American Surgeon*, Apr. 1992, 58:232-238.

Molgaard, C. P. et al. "Access-Site Thrombosis after Placement of Inferior Vena Cava Filters with 12-14 F Delivery Sheaths," *Radiology* 1992, 185:257-261.

Moors, A. H. et al. "Convective Warming After Hypothermic Cardiopulmonary Bypass," *British Journ. of Anesth.*, 1994, 73:782-785.

Moors, A. H. et al. "Convective Warming after Hypothermic Cardiopulmonary Bypass," *Brit. Journ. Anaesth.* 1994; 73-782-785.

Ferris, E. J. et al. "Percutaneous Inferior Vena Caval Filters: Follow-up of Seven Designs in 320 Patients," *Radiology*, Sep. 1993, 188(3):851-856.

Frank, S. M. et al. "Perioperative Maintenance of Normothermia Reduces the Incidence of Morbid Cardiac Events" *JAMA* Apr. 9, 1997, 277(14):1127-1134.

Goldman, B. S. et al. "Complications Associated with Use of the Intra-Aortic Balloon Pump," *The Canadian Journal of Surgery*, Mar. 1982, 25(2):153-156.

Greenfield, L. J. and A. DeLucia III et al. "Endovascular Therapy of Venous Thromboembolic Disease," Endovascular Surgery: *Surgical Clinics of North America*, 1992, 72(4):969-989.

Greenfield, L. J. et al. "Results of a Multicenter Study of the Modified Hook-Titanium Greenfield Filter," *Journal of Vascular Surgery*, Sep. 1991, 14(3):253-257.

Grollman, J. H. "Complications of Pulmonary Arteriography," *Seminars in Interventional Radiology*, Jun. 1994, 11(2):113-120.

Hanhela, R. et al. "The Effects of Two Rewarming Strategies on heat Balance and Metabolism after Coronary Artery Bypass Surgery with Moderate Hypothermia," Acta Anaesthesiol. Scand., 1999, 43:979-988.

Heintzen, M. P. and B. E. Strauer, "Peripheral Arterial Complications after Heart Catheterization," *Herz* 1998, 23(1):4-20.

Hessel, S. J. et al. "Complications of Angiography," *Diagnostic Radiology*, Feb. 1981, 138:273-281.

Horowitz, M. B. et al. "Assessment of Complication Types and Rates Related to Diagnostic Angiography and Interventional Neuroradiologic Procedures," *Interventional Neuroradiology*, 1998, 4:27-37.

Insler, S. R. et al. "Association Between Postoperative Hypothermia and Adverse Outcome after Coronary Artery Bypass Surgery," *Soc. Thorac. Surg.* 2000; 70:175-81.

Janke, E. L. "Evaluation of Two Warming Systems after Cardiopulmonary Bypass," *Brit. Journ. Anaesth.* 1996; 77:268-270.

Mora, C. T. et al. "The Effect of Temperature Management During Cardiopulmonary Bypass on Neurologic and Neuropsychologic Outcomes in Patients Undergoing Coronary Revascularization," Aug. 1966, 112(2):514-522.

Noto, T. J. et al. "Cardiac Catheterization 1990: A Report of the Registry of the Society for Cardiac Angiography and Interventions (SCA&I)," *Catheterization and Cardiovascular Diagnosis*, 1991, 24:75-83.

Holzer, M., W. Behringer, W. Schörkhuber, A. Zeiner, F. Sterz, A. N. Laggner, M. Frass, P. Siostrozonek, K. Ratheiser, and A.Kaff, "Mild Hypothermia and Outcome after CPR," *Cardiopulmonary and Cerebral Resuscitation: An Update*, HACA Study Group, 55-58.

Lustgarten, D. L., D. Keane, and J. Ruskin, "Cryothermal Ablation: Mechanism of Tissue Injury and Current Experience in the Treatment of Tachyarrhythmias," *Progress in Cardiovascular Diseases*, vol. 41, No. 6 , pp. 481-498 (May/Jun. 1999).

Pujol, A. et al. Afterdrop After Cardiopulmonary Bypass: The Value of Tempanic Membrane Temperature Monitoring,: *Journ. of Cardiothoracic and Vascular Anesth.*, Apr. 1966, 10(3):326-341.

Kinney, Thomas B., et al.; Optimizing Myocardial Hypothermia: I. Temperature Probe Design and Clinical Inferences; Ann Thorac Surg; vol. 51; pp. 278-283 (1991).

Mazala, M., et al.; Hypothermia and the Action of Neuromuscular Blocking Agents; Anaesthesia; vol. 43; Issue No. 2; p. 162 (Feb. 1988).

Osgusthorpe, Susan G., et al.; Hypothermia and Rewarming after Cardiac Surgery; AACN Clin Issues Crit Care Nurs; vol. 4; No. 2; pp. 276-292 (May 1993).

Wakida, et al.; Percutaneous Cooling of Ischemic Myocardium by Hypothermic Retroperfusion of Autologous Arterial Blood: Effects on Regional Myocardial Temperature Distribution and Infarct Size; JACC; vol. 18; No. 1; pp. 293-300 (Jul. 1991).

Dubuc, M., M. Talajic, D. Roy, B. Thibault, T. Ki Leung, K. Spector, P. Friedman, "Catheter Cryoablation: A Novel Technology for Ablation of Cardiac Arrhythmias," *Abstracts from the 69th Scientific Session,*—I-557 No. 3259.

Frank, S. M., P. Satitpunwaycha, S.R. Bruce, C. Holmes, S. Brentzel, D. S. Goldstein, "Sympoathoneural and Adrenomedullary Responses to Decreased Core Temperature in Awake Humans," *Abstract presented Oct. 2000 in Puerto Rico at Annual Meeting of the American Autonomic Society—Not Yet Published.*

Sani, G., F. Benetti, M. A. Mariani, G. Lisi, M. Maccherini, M. Toscano, "Arterial Myocardial Revascularization without Cardiopulmonary Bypass through a Small Thoracotomy," *Eur. J. Cario-Thorac. Surg.* 10:699-701 (1996).

AVECOR Cardiovascular Inc., "BIOtherm Heat Exchanger Instruction Manual," Jul. 1991, 4 pages.

Bone, M. E. and R. O. Feneck, "Bladder Temperature as an Estimate of Body Temperature during Cardiopulmonary Bypass," *Anaesthesia*, 1988, 43:181-185.

Chan, L. L. et al. "Radiological Placement of 211 Central Venous Catheters: outcome and Complications," *Ann. Acad. Med. Singapore*, Jul. 1999, 28(4):481-487.

Cobos, E. et al. "Prevention and Management of Central Venous Catheter Thrombosis," *Curr. Opin. Hematol.* Sep. 1998, 5-9.

Cook, L. et al. "Intra-Aortic Balloon Pump Complications: A Five-Year Retrospective Study of 283 Patients," *Heart & Lung*, May/Jun. 1999, 28(3):195-202.

Davidson, J. et al. "Intra-Aortic Balloon Pump: Indications and Complications," *Journal of the National Medical Association*, 90(3):137-140.

Deakin, C. D. et al. "Thermal Energy Balance as a Measure of Adequate Rewarming from Hypothermic Cardiopulmonary Bypass," *Journ. of Cardiothoracic and Vascular Anesth.*, Aug. 2000, 14(4):388-392.

Dodek, A. et al. "Complications of Coronary Arteriography," *Can. Med. Assoc. J.*, Apr. 15, 1983, 128:934-936.

El-Rahmany, H. K. et al. "Determinants of Core Temperature at the Time of Admission to Intensive Care Following Cardiac Surgery," *Journ. Clin. Anesth.* 2000, 12:177-183.

Elrifai, A. M. et al, "Rewarming, Ultraprofound Hypothermia and Cardiopulmonary Bypass," Mar. 13-16, 1992, *Journ. of Extra-Corporeal Tech.*, 24(4):107-112.

Feliciano, D. V. et al. "Metabolic and Nutritional Support by F. B. Cerra," *Trauma 3rd Ed.* 1996, Chapter 62, 1155-1176.

Hederer, G., et al.; "Animal Experiment Observations Regarding Cardiac Surgery under Intravascular Hypothermia"; Labgebbecjs Arch. U. Dtsch. A. Chir., Bd. 283, S. 601-625 (1957) (German article with English translation).

Behmann, F.W; "Heat Generation Control during Artificial Hypothermia: II. Theoretical Examinations"; Pflügers Archiv, Bd. 266, S. 422-446 (1958) (German article with English translation).

Behmann, F.W., et al; << Heat Generation Control during Artificial Hypothermia: I: Experimental Examination of the Influence of Anesthetic Depth; Pflügers Archiv, Bd. 266, S. 408-421 (1958) (German article with English translation).

Behmann, F.W., et al.; Intravascular Cooling, a Method to Achieve Controllable Hypothermia; Pflügers Archive, vol. 263, pp. 145-165 (1956) (German article with English translation).

Jackson, Donald, et al; "Hypothermia : IV. Study of Hypothermia Induction Time with Various Pharmacological Agents (24617)"; Proc Soc Exp Biol Med.; 100(2): 332-335 (Feb. 1959).

Behmann, F.W.; "Heat Generation Control during Artificial Hypothermia, an article about the economic problem of trembling stages"; Pflügers Archive, vol. 263, pp. 166-187 (1956) (German article with English translation).

Behmann, F.W.; "Regulation of heat production in experimental hypothermia of homothermal animals"; Naunyn Schmiedebergs Arch Exp Pathol Pharmakol; 228 (1-2): 126-128 (1956) (German-article with English translation).

Coronary Hemodynamic Effects of Hemopump, AmHeart J, 1998, 135(5), pp. 844-849. Abstract Only.

Medtronic, Inc., Medtronic Begins U.S. Clinical Testing of Pump to Facilitate Minimally Invasive Heart Bypass Surgery, Press Release, Jan. 20, 1997. www.medtronic.com.

Michael S. Sweeney, MD., "The Hemopump in 1997: A Clinical, Political and Marketing Evolution", *Annals of Thoracic Surgery*, 1999, vol. 68, pp. 761-763.

Corvascular, Inc. Company Profile, www.corvascular.com.

Jessen, et at, "Intravascular Heat Exchanger for Conscious Goats", 1977.

Mercer, et al., "Effects of Total Body Core Cooling on Heat Production of Conscious Goats", 1978.

Williams, et al., "Passivity Breakdown and Pitting Corrosion of Binary Alloys", 1991.

Metra, MD., et al., "A Rationale for the Use of Beta-Blockers as a Standard Treatment for Heart Failure", *AM Heart J*, 2000, 139(3), pp. 511-521.

S. Westaby, "Coronary Surgery Without Cardiopulmonary Bypass", *British Heart Journal*, Mar. 1995, 73(3), pp. 203-205.

Benetti, et al. Direct Myocardial Revascularization Without Extraxcorporeal Circulation. Experience in 700 Patients, Chest, Aug. 1991, 100(2), pp. 312-316.

Pfister, et al., "Coronary Artery Bypass Without Cardiopulmonary Bypass", *Annals of Thoracic Surgery*, Dec. 1992, 54(6), pp. 1085-1092.

Fanning, et al., "Reoperative Coronary Artery Bypass Grafting Without Cardiopulmonary Bypass", *Annals of Thoracic Surgery*, 1993, vol. 55, pp. 486-489.

Coimbra, et al., Long Lasting Neuroprotective Effect of Postischemic Hypothermia and treatment with an Anti-Inflammatory/Antipyretic Drug, Stroke, 1996, 27(9), pp. 1578-1585.

*Primary Examiner* — Roy D Gibson

(57) ABSTRACT

The use of an intravascular cooling element to induce hypothermia in connection with a medical procedure. According to a first aspect of the present, invention, a coronary bypass procedure is conducted in which a patient's blood is oxygenated with the patient's lungs and in which blood is circulated using the patient's heart or using an intracorporeal pump. The procedure preferably comprises: (a) positioning a heat transfer element in a blood vessel of a patient; (b) cooling the body of the patient to less than 35° C., more preferably 32±2° C., using the heat transfer element; and (c) forming a fluid communicating graft between an arterial blood supply and the coronary artery. The body of the patient is preferably heated to about 37° C. using the heat transfer element subsequent to the step of forming the fluid communicating graft. According to a further aspect of the invention, a hypothermic medical procedure is provided while a patient is in a conscious or semiconscious state, comprising (a) administering a beta-blocking drug to the patient; (b) delivering a heat transfer element to a blood vessel of the patient; and (c) cooling a region of the patient or the body of the patient to less than 35° C. using the heat transfer element.

10 Claims, 7 Drawing Sheets

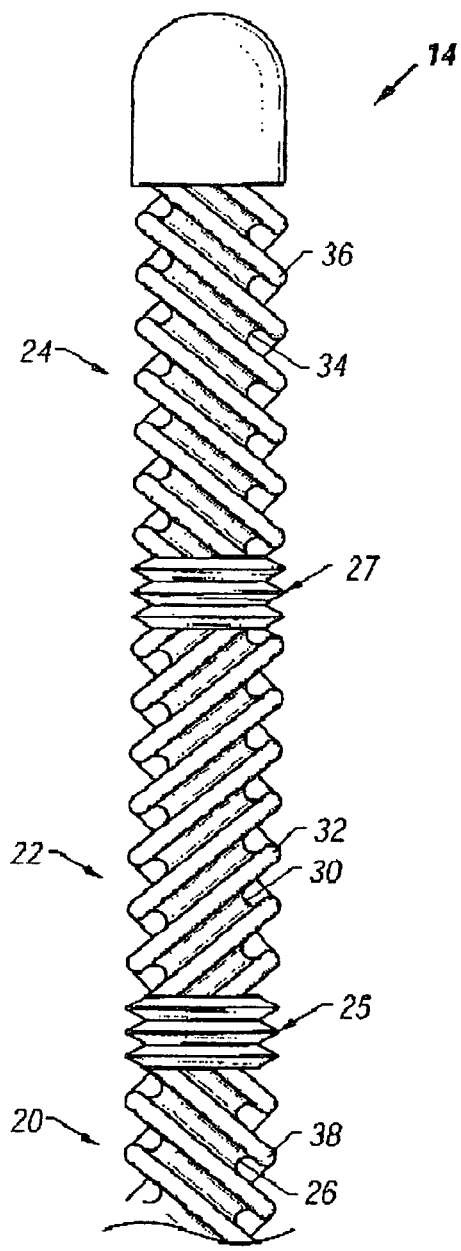
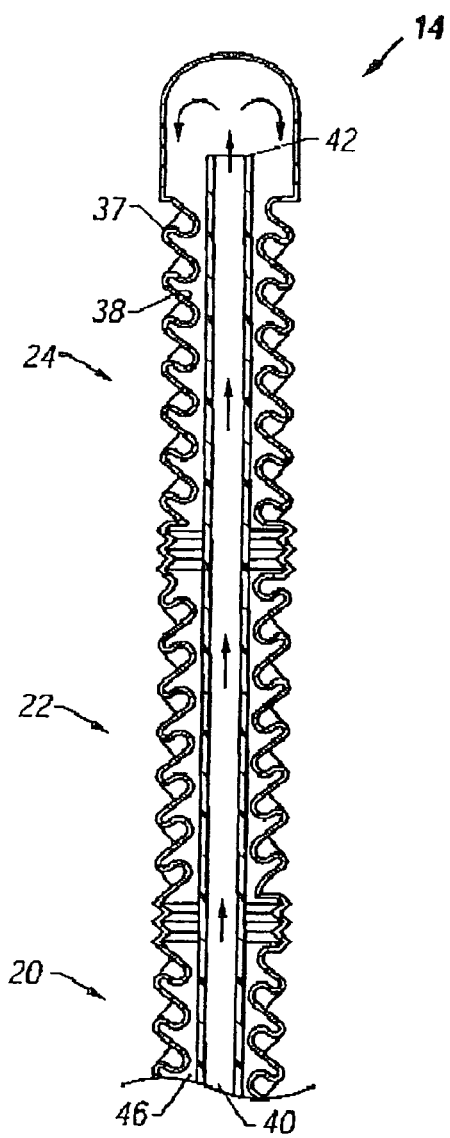
FIG. 3
FIG. 4

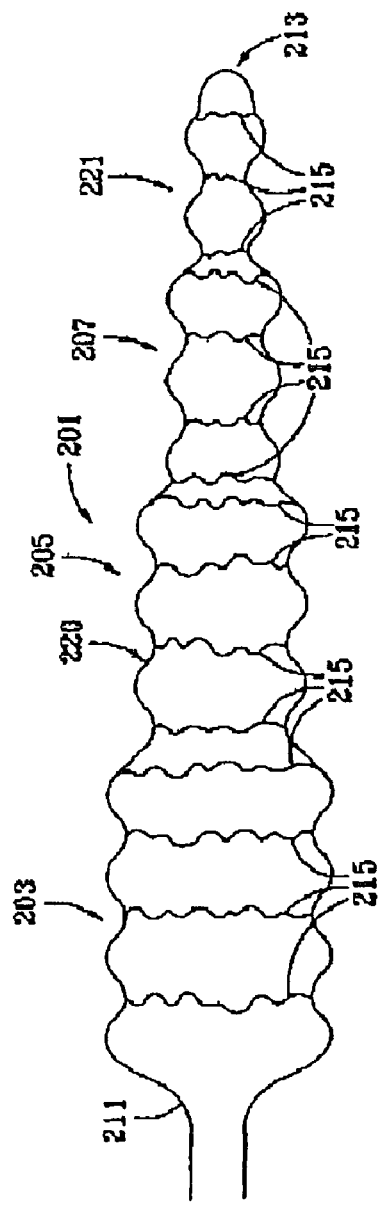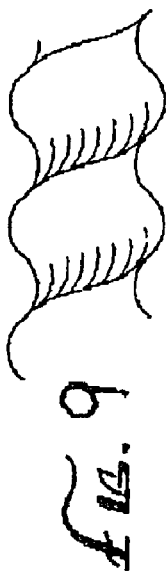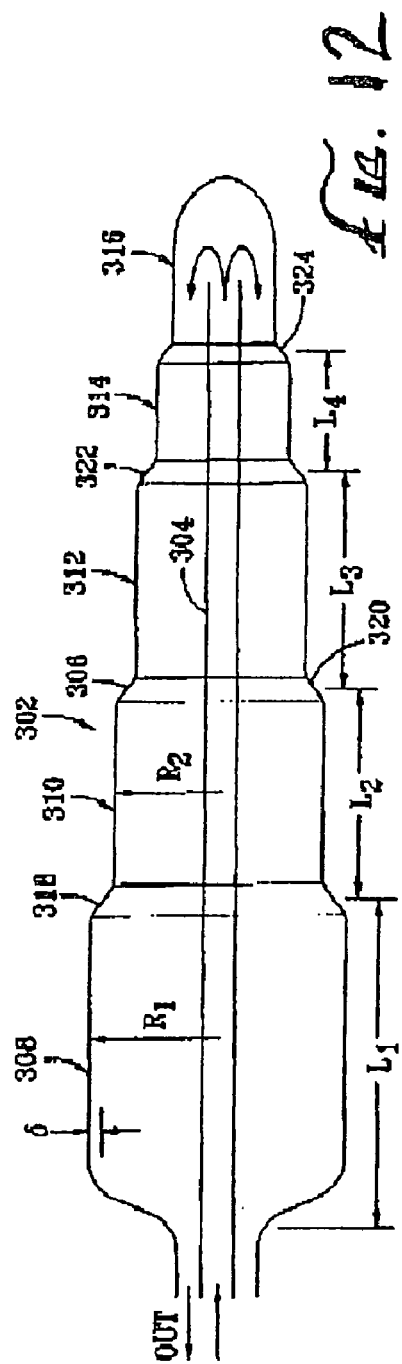

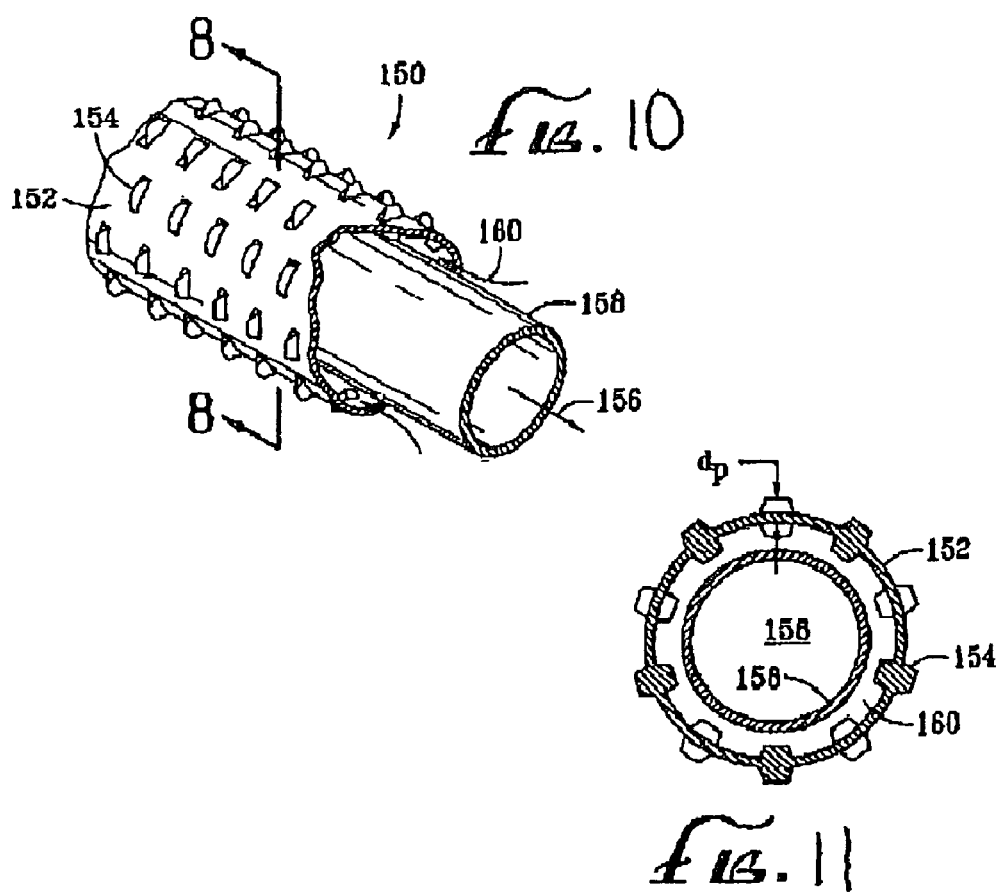

MEDICAL PROCEDURE

STATEMENT OF RELATED APPLICATIONS

This application is divisional of U.S. patent application Ser. No. 10/934,096, filed Sep. 3, 2004, entitled "Medical Procedure", now U.S. Pat. No. 7,371,254, which is a continuation-in-part of U.S. patent application Ser. No. 10/714,070, filed Nov. 14, 2003, now abandoned, and a continuation in part of U.S. patent application Ser. No. 10/008,999, filed Dec. 7, 2001, now U.S. Pat. No. 6,786,218.

Said Ser. No. 10/714,070 is a continuation of U.S. patent application Ser. No. 10/095,753, filed Mar. 11, 2002, now U.S. Pat. No. 6,695,873, which is a divisional of U.S. patent application Ser. No. 09/757,124, filed Jan. 8, 2001, now U.S. Pat. No. 6,540,771, which is a divisional of U.S. patent application Ser. No. 09/215,038, filed Dec. 16, 1998, now U.S. Pat. No. 6,261,312, which is a continuation-in-part of U.S. patent application Ser. No. 09/103,342, filed Jun. 23, 1998, now U.S. Pat. No. 6,096,068, which is a continuation-in-part of U.S. patent application Ser. No. 09/047,012, filed Mar. 24, 1998, now U.S. Pat. No. 5,957,963, which is a continuation-in-part of U.S. patent application Ser. No. 09/012,287, filed Jan. 23, 1998, now U.S. Pat. No. 6,051,019.

Said Ser. No. 10/008,999 is a divisional of U.S. patent application Ser. No. 09/539,932, filed Mar. 31, 2000, now U.S. Pat. No. 6,491,039, which is a continuation-in-part of U.S. patent application Ser. No. 09/306,866, filed May 7, 1999, now U.S. Pat. No. 6,235,048, which is a divisional of U.S. patent application Ser. No. 09/012,287, filed Jan. 23, 1998, now U.S. Pat. No. 6,051,019.

Said Ser. No. 09/539,932 is also a continuation-in-part of U.S. patent application Ser. No. 09/373,112, filed Aug. 11, 1999, now U.S. Pat. No. 6,843,800, which is a continuation-in-part of U.S. patent application Ser. No. 09/292,532, filed Apr. 15, 1999, now abandoned, which is a continuation-in-part of U.S. patent application Ser. No. 09/103,342, filed Jun. 23, 1998, now U.S. Pat. No. 6,096,068 and a continuation-in-part of U.S. patent application Ser. No. 09/052,545, filed Mar. 31, 1998, now U.S. Pat. No. 6,231,595 and a continuation-in-part of U.S. patent application Ser. No. 09/047,012, filed Mar. 24, 1998, now U.S. Pat. No. 5,957,963, which is a continuation-in-part of U.S. patent application Ser. No. 09/012,287, filed Jan. 23, 1998, now U.S. Pat. No. 6,051,019.

Each of the prior disclosures is incorporated herein by reference in its entirety.

FIELD OF THE INVENTION

The present invention relates to the use of an intravascular cooling element to induce hypothermia in connection with medical procedures.

BACKGROUND OF THE INVENTION

A number of approaches have been developed for treating coronary artery disease. In less severe cases, it is often sufficient to merely treat the symptoms with pharmaceuticals or to treat the underlying causes of the disease with lifestyle modification. In more severe cases, the coronary blockage can be treated endovascularly or percutaneously using techniques such as balloon angioplasty, atherectomy, laser ablation, stents, and the like.

In cases where these approaches have failed or are likely to fail, it is often necessary to perform a coronary artery bypass graft procedure ("coronary bypass procedure"). In this procedure, direct access to the heart is first achieved. This is usually done by opening the chest by median sternotomy and spreading the left and right rib cage apart. The pericardial sac is then opened to achieve direct access to the heart. Next, a blood vessel or vessels for use in the graft procedure are mobilized from the patient. This usually entails mobilizing either a mammary artery or a saphenous vein, although other graft vessels may also be used.

A heart-lung or cardiopulmonary bypass is then performed. This procedure usually entails arterial and venous cannulation, connecting the bloodstream to a cardiopulmonary bypass system, cooling the body to about 32 degrees Celsius, cross clamping the aorta, and cardioplegic perfusion of the coronary arteries to arrest and cool the heart to about 4 degrees Celsius.

The arrest or stoppage of the heart is generally carried out because the constant pumping motion of the beating heart makes surgery upon the heart difficult. Cooling the body protects the organs from ischemia (a condition in which a tissue or organ does not receive a sufficient supply of blood), reduces the cardiac output requirement, and increases the systemic vascular resistance, which helps maintain perfusion and reduces the cardiopulmonary circuit primary volume.

Once cardiac arrest is achieved, a graft (or grafts) is attached to the relevant portions of a coronary artery (or arteries) followed by weaning from the cardiopulmonary bypass, restarting the heart, and decannulation. Finally the chest is closed.

After arresting the heart, the heart muscle, or myocardium, is protected and supported so that it does not suffer cellular or nerve damage that would prevent the heart from working properly when it is started again. There are two important aspects to the process of myocardial protection: (1) reducing the oxygen demand of the heart muscle; and (2) adequately oxygenating the heart muscle and maintaining the proper chemical balance so that cellular damage does not occur. One common technique for doing so is known as cold cardioplegia.

During this procedure, the coronary arteries must be isolated to prevent reperfusion of the myocardium with warm oxygenated blood from the cardiopulmonary bypass system that would wash out the cardioplegic agent and prematurely start the heart beating again. The most common way to isolate the coronary arteries is by aortic cross clamping, which is normally implemented in the following fashion. Before stopping the heart, the patient is prepared by placement of an arterial cannula and a venous cannula, which are connected to the cardiopulmonary bypass system. The cardiopulmonary bypass system takes over the functions of the heart and the lungs of the patient by pumping and oxygenating the blood while the heart is stopped. Once the cardiopulmonary bypass system is connected and started, the ascending aorta can be cross-clamped to isolate the coronary arteries from the rest of the systemic arterial circulation. Then, cardioplegic arrest is induced by injecting 500-1000 cc of cardioplegic solution into the aortic root using a needle or cannula which pierces the wall of the ascending aorta upstream of the cross clamp.

Unfortunately, significant complications may result from such procedures. For example, application of an external cross-clamp to a calcified or atheromatous aorta may cause the release of emboli into the brachiocephalic, carotid or subclavian arteries with serious consequences such as strokes.

Systems have been proposed in which the aorta is occluded without cross clamping. For example, U.S. Pat. No. 5,957,879 describes systems that include an aortic occlusion device having a balloon to occlude the ascending aorta and a lumen to deliver cardioplegic fluid for arresting the patient's heart.

The aortic occlusion device replaces the conventional external cross-clamp and is said to reduce the amount of displacement and distortion of the aorta. Nonetheless, distortion is not eliminated, and the risk of emboli release remains present.

Other complications can arise from the cardiopulmonary bypass system, which includes mechanical blood pumps, an oxygenator, a heat exchanger, blood reservoirs and filters, and several feet of tubing to transport the blood from the patient on the operating table to the heart-lung machine located nearby and back to the patient. Such systems can cause complications due to the exposure of blood to foreign surfaces, which result in the activation of virtually all the humoral and cellular components of the inflammatory response, as well as some of the slower reacting specific immune responses. Other complications from cardiopulmonary bypass include loss of red blood cells and platelets due to shear stress damage. In addition, cardiopulmonary bypass requires the use of an anticoagulant, such as heparin. This may, in turn, increase the risk of hemorrhage. Finally cardiopulmonary bypass sometimes necessitates giving additional blood to the patient. The additional blood, if from a source other than the patient, may expose the patient to blood-borne diseases.

Due to the risks noted above, others have attempted to perform a coronary artery bypass graft procedure without occluding the aorta and without cardiopulmonary bypass. For example, attempts have been made wherein surgery is performed on a beating heart. The technique of operating on the beating heart, however, is difficult, due to the rapid movement of the heart, and can at present only be applied to single vessel bypassing procedures. Moreover, partial aortic cross clamping is generally implemented, which can dislodge emboli.

In other reported procedures, surgeons have been experimenting with a technique that involves stopping or nearly stopping the heart and supporting circulation with a small pump positioned in the patient's vasculature (i.e., an intracorporeal pump). See, for example, M. S. Sweeney, "The Hemopump in 1997: A Clinical, Political, and Marketing Evolution", *Ann. Thorac. Surg.*, 1999, Vol. 68, pp. 761-3 in which a coronary bypass procedure is described that uses a Medtronic Hemopump® for circulatory support and the patient's own lungs from oxygenation. Esmolol, a short acting beta-blocker, was administered to make the heart more tranquil during surgery. The interior surface area of the Hemopump is greatly reduced relative to traditional cardiopulmonary bypass systems, reducing the complications of such surfaces.

Unfortunately, it can be difficult to provide adequate circulation with a pump of this type, increasing the risk of ischemia. Moreover, while many of the dangers associated with cardiopulmonary bypass systems are avoided, certain benefits of such a system are also lost. For example, hypothermia is no longer induced in the patient, which serves to lower oxygen demand and which induces vasoconstriction, supporting perfusion. Each of these effects serves to protect the organs from ischemic damage.

Still other techniques have been proposed in which the heart is stopped or nearly stopped (e.g., placed in a reversible, temporary heart block) by locally delivering drugs, such as beta-blockers. At the same time, the heart is continuously paced by external pacemaker stimulation. In this way, alternating periods of heartbeat and heart arrest (e.g., up to 15 seconds) can be established, providing the surgeon with short intervals in which he or she can work on a stilled heart without resorting to a pump for supporting circulation. One such system is the TRANSARREST system of Corvascular, Inc., Palo Alto, Calif. Still other methods are known in which surgery is facilitated by stopping or slowing the heart though electrical stimulation of the vagus nerve. See, e.g., U.S. Pat. Nos. 5,913,876 and 6,006,134.

Unfortunately, as in the above case wherein the Hemopump supports circulation, these techniques result in less than ideal circulation and do not provide a hypothermic effect, increasing the risk of ischemia.

Medical procedures are also known in which hypothermia is induced in a conscious or semiconscious person, for example, where hypothermia is induced in a stroke victim to reduce ischemic damage. However, in such patients, hypothermia activates the sympathetic nervous system, resulting in a significant norepinephrine response. Norepinephrine, in turn, binds to beta-receptor sites, including those in the heart, causing the heart to beat harder and more rapidly, frequently resulting in cardiac arrythmia and increasing the risk of myocardial ischemia. Norepinephrine also causes peripheral vasoconstriction, frustrating relief of patient discomfort, for example, by using heating blankets.

SUMMARY OF THE INVENTION

The above and other difficulties associated with the prior art are addressed by the present invention.

According to a first aspect of the present invention, a coronary bypass procedure is conducted in which the patient's blood is oxygenated with the patient's lungs and in which blood is circulated using the patient's heart or using an intracorporeal pump. The procedure preferably comprises: (a) positioning a heat transfer element in a blood vessel of a patient; (b) cooling the body of the patient to less than 35° C., more preferably 32±2° C., using the heat transfer element; and (c) forming a fluid communicating graft between an arterial blood supply and the coronary artery.

The body of the patient is desirably heated to about 37° C. using the heat transfer element subsequent to the step of forming the fluid communicating graft.

Numerous variations are possible. For example, the step of forming a fluid communicating graft between the arterial blood supply and the coronary artery can be performed on a beating heart during bradycardia of the heart that occurs upon cooling the patient's body.

In another embodiment, the heart can be arrested or nearly arrested during at least a portion of the step of forming the fluid communicating graft. For example, the heart can be chemically arrested (e.g., using one or more beta-blockers), or the heart can be electrically arrested. While heart is arrested, the patient's circulation is preferably supported with a pump positioned in the patient's vasculature. In a preferred embodiment, the pump is at least partially positioned in the left ventricle and is introduced into the patient through the femoral artery.

In yet another embodiment, the heartbeat is intermittently arrested and stimulated, and at least a portion of the step of forming the fluid communicating graft is carried out during periods of heartbeat arrest. For example, the heart can be chemically arrested (e.g., with one or more beta blockers) and electrically stimulated. Alternatively, the heart can be both electrically arrested and electrically stimulated. In this way, the use of a pump can be avoided.

The heat transfer element can be positioned, for example, in the venous vasculature, where it is preferably introduced via the femoral vein. More preferably, the heat transfer element is positioned in the inferior vena cava via the femoral vein. In this instance, the heat transfer element is preferably about 4 to 5 mm in diameter.

In one preferred embodiment, the heat transfer element is attached to the distal end of a flexible catheter, and the catheter is used in the step of positioning the heat transfer element in the blood vessel. The catheter is also used to convey chilled or heated fluid to the interior of the heat transfer element.

The catheter is desirably configured for efficient heat transfer. As an example, it is preferred that the heat transfer element absorbs at least 150 Watts of heat during cooling. To promote efficient heat transfer, the heat transfer element can comprise a plurality of exterior and interior surface irregularities, wherein the exterior and interior surface irregularities are preferably shaped and arranged to create mixing in the blood and in the fluid within the heat transfer element, respectively. In a preferred embodiment, the interior and exterior surface irregularities comprise one or more helical ridges and one or more helical grooves.

In one embodiment, the heat transfer device has a high degree of lateral flexibility and is collapsible, thereby affording an easy insertion procedure. The device allows high surface area to increase heat transfer.

In one aspect, the invention is directed to a catheter system to change the temperature of blood by heat transfer to or from a working fluid. The system includes an inflatable inlet lumen and outlet lumen. The outlet lumen is coupled to the inlet lumen so as to transfer working fluid between the two. The outlet lumen has a structure when inflated to induce turbulence in the blood and/or in the working fluid.

Variations of the system may include one or more of the following. The inlet lumen and the outlet lumen may be made of a flexible material such as latex rubber. The outlet lumen may have a structure to induce turbulence in the working fluid when inflated, such as a helical shape which may be tapered in a segmented or non-segmented manner. The radii of the inlet and outlet lumens may decrease in a distal direction such that the inlet and outlet lumens are tapered when inflated. A wire may be disposed in the inlet or outlet lumens to provide shape and strength when deflated.

The thickness of the outlet lumen, when inflated, may be less than about ½ mil. The length of the inlet lumen may be between about 5 and 30 centimeters. If the outlet lumen has a helical shape, the diameter of the helix may be less than about 8 millimeters when inflated. The outer diameter of the helix of the outlet lumen, when inflated, may be between about 2 millimeters and 8 millimeters and may taper to between about 1 millimeter and 2 millimeters. In segmented embodiments, a length of a segment may be between about 1 centimeter and 10 centimeters. The radii of the inlet and outlet lumens when inflated may be between about 0.5 millimeters and 2 millimeters.

The outlet lumen may further include at least one surface feature and/or interior feature, the surface feature inducing turbulence in the fluid adjacent the outlet lumen and the interior feature inducing turbulence in the working fluid. The surface feature may include one or more helical turns or spirals formed in the outlet lumen. Adjacent turns may employ opposite helicity. Alternatively or in combination, the surface feature may be a series of staggered protrusions formed in the outlet lumen.

The turbulence-inducing outlet lumen may be adapted to induce turbulence when inflated within a free stream of blood when placed within an artery. The turbulence intensity may be greater than about 0.05. The turbulence-inducing outlet lumen may be adapted to induce turbulence when inflated throughout the period of the cardiac cycle when placed within an artery or during at least 20% of the period.

The system may further include a coaxial supply catheter having an inner catheter lumen coupled to the inlet lumen and a working fluid supply configured to dispense the working fluid and having an output coupled to the inner catheter lumen. The working fluid supply may be configured to produce a pressurized working fluid at a temperature of between about −3° C. and 36° C. and at a pressure below about 5 atmospheres of pressure. Higher temperatures may be employed if blood heating is desired.

The turbulence-inducing outlet lumen may include a surface coating or treatment such as heparin to inhibit clot formation. A stent may be coupled to the distal end of the inlet lumen. The system may be employed to cool or heat volumes of tissue rather than blood.

In embodiments employing a tapered helical outlet lumen, the taper of the outlet lumen allows the outlet lumen to be placed in an artery having a radius less than the first radius. The outlet lumen may be tapered in segments. The segments may be separated by joints, the joints having a radius less than that of either adjacent segment.

In another aspect, the invention is directed to a method of changing the temperature of blood by heat transfer. The method includes inserting an inflatable heat transfer element into an artery or vein and inflating the same by delivering a working fluid to its interior. The temperature of the working fluid is generally different from that of the blood. The method further includes inducing turbulence in the working fluid by passing the working fluid through a turbulence-inducing path, such that turbulence is induced in a substantial portion of a free stream of blood. The inflatable heat transfer element may have a turbulence-inducing structure when inflated.

In another aspect, the invention is directed towards a method of treating the brain which includes inserting a flexible heat transfer element into an artery from a distal location and circulating a working fluid through the flexible heat transfer element to inflate the same and to selectively modify the temperature of an organ without significantly modifying the temperature of the entire body. The flexible, conductive heat transfer element preferably absorbs more than about 25, 50 or 75 watts of heat. The artery may be the common carotid or a combination of the common carotid and the internal carotid.

In another aspect, the invention is directed towards a method for selectively cooling an organ in the body of a patient which includes introducing a catheter into a blood vessel supplying the organ, the catheter having a diameter of 5 mm or less, inducing free stream turbulence in blood flowing over the catheter, and cooling the catheter to remove heat from the blood to cool the organ without substantially cooling the entire body. In one embodiment, the cooling removes at least about 75 watts of heat from the blood. In another embodiment, the cooling removes at least about 100 watts of heat from the blood. The organ being cooled may be the human brain.

The circulating may further include passing the working fluid in through an inlet lumen and out through an outlet, coaxial lumen. The working fluid may be a liquid at or well below its boiling point, and furthermore may be aqueous.

Advantages of the invention include one or more of the following. The design criteria described above for the heat transfer element: small diameter when deflated, large diameter when inflated, high flexibility, and enhanced heat transfer rate through increases in the surface of the heat transfer element and the creation of turbulent flow, facilitate creation of a heat transfer element which successfully achieves selective organ cooling or heating. Because only a selected organ is cooled, complications associated with total body hypothermia are avoided. Because the blood is cooled intravascularly, or in situ, problems associated with external circulation of the blood are eliminated. Also, only a single puncture and arterial vessel cannulation are required which may be performed at an easily accessible artery such as the femoral, subclavian, or brachial arteries. By eliminating the use of a cold perfusate, problems associated with excessive fluid accumulation are avoided. In addition, rapid cooling to a precise temperature may be achieved. Further, treatment of a patient is not cumbersome and the patient may easily receive continued care during the heat transfer process. The device and method may be easily combined with other devices and techniques to provide aggressive multiple therapies. Other advantages will become clear from the description below.

According to a second aspect of the invention, a hypothermic medical procedure is provided comprising (a) administering a beta-blocking drug to a patient; (b) delivering a heat transfer element to a blood vessel of a patient; and (c) cooling a region of the patient or the body of the patient to less than 35° C. using the heat transfer element while the patient is in a conscious or semiconscious state. Preferably, the beta-blocking drug is administered after delivering the heat transfer element to the blood vessel. Preferred beta-blocking drugs for this aspect of the invention include β1 blockers, β1β2 blockers, and αβ1β2 blockers. Preferred β1 blockers include acebutolol, atenolol, betaxolol, bisoprolol, esmolol and metoprolol. Preferred β1β2 blockers include carteolol, nadolol, penbutolol, pindolol, propranolol, sotalol and timolol. Preferred αβ1β2 blockers include carvedilol and labetalol.

Advantages of the present invention include the elimination of aortic occlusion and cardiopulmonary bypass systems during coronary bypass surgery. Where beating heart procedures are incorporated, another advantage of the present invention is the promotion of a bradycardia of the heart, simplifying surgery.

Another advantage of the present invention include a reduction in the risk of ischemia associated with techniques that provide circulatory flow rates that are significantly lower than ordinary cardiac output and with techniques incorporating vasodilatory substances.

Yet another advantage of the present invention is that the risk of cardiac arrythmia and myocardial ischemia is reduced in connection with medical procedures that induce hypothermia in conscious or semiconscious patents.

The above and other embodiments and advantages of the invention will become apparent to those of ordinary skill in the art upon reading the description and claims to follow.

BRIEF DESCRIPTION OF THE DRAWINGS

FIG. 3 is an elevation view of a heat transfer element used in accordance with an embodiment of the invention.

FIG. 4 a longitudinal section view of the heat transfer element of FIG. 3.

FIG. 8 illustrates a turbulence-inducing heat transfer element according to a second alternative embodiment of the invention employing a surface area enhancing taper and turbulence-inducing surface features.

FIG. 9 illustrates a type of turbulence-inducing surface feature which may be employed in the heat transfer element of the embodiment of FIG. 8. In FIG. 9 a spiral feature is shown.

FIG. 10 illustrates another type of turbulence-inducing surface feature which may be employed in the heat transfer element of the embodiment of FIG. 8. In FIG. 10, a series of staggered protrusions are shown.

FIG. 11 is a transverse cross-sectional view of the heat transfer element of the embodiment of FIG. 10.

FIG. 12 illustrates a heat transfer element according to a third alternative embodiment of the invention employing a surface area enhancing taper.

DETAILED DESCRIPTION OF THE INVENTION

The present invention now will be described more fully hereinafter. This invention may, however, be embodied in different forms and should not be construed as limited to the embodiments set forth herein.

According to one aspect of the present invention, a procedure is provided by which a surgeon is able to perform a coronary bypass procedure with hypothermic protection, while at the same time avoiding many of the disadvantages associated with the use of traditional external cardiopulmonary bypass systems and aortic clamping procedures.

In one embodiment of the present invention, a heat transfer element is provided within a blood vessel of the body such that blood is cooled in vivo upon contact with the heat transfer element.

The heat transfer element can be provided in either arterial or venous blood vessels. One preferred location for the heat transfer element is the inferior vena cava, which typically ranges from 15 mm to 25 mm in diameter. A preferred method by which the heat transfer element is provided at this position is via entry at the femoral vein.

Figure 1:
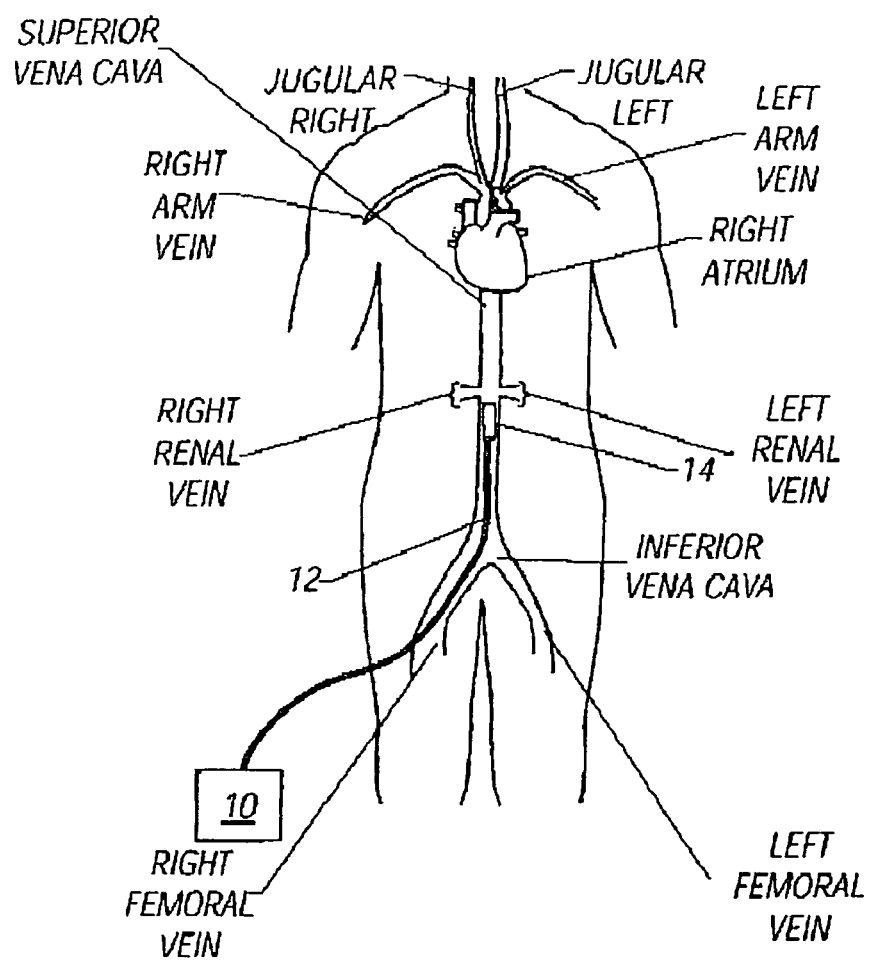
FIG. 1 is a schematic representation of the use of a heat transfer element to cool the body, according to an embodiment of the invention.

FIG. 1 is a schematic representation of the use of a heat transfer element in cooling the body of a patient. The apparatus shown in FIG. 1 includes a working fluid supply 10, preferably supplying a chilled aqueous solution, a supply catheter 12 and a heat transfer element 14. The supply catheter 12 may have a substantially coaxial construction. An inner coaxial lumen within the supply catheter 12 receives coolant from the working fluid supply 10. The coolant travels the length of the supply catheter 12 to the heat transfer element 14 that serves as the cooling tip of the catheter. At the distal end of the heat transfer element 14, the coolant exits an insulated interior lumen and traverses the length of the heat transfer element 14 in order to decrease the temperature of the surface of the heat transfer element 14. The coolant then traverses an outer lumen of the supply catheter 12 so that it may be disposed of or recirculated. The supply catheter 12 is a flexible catheter having a diameter sufficiently small to allow its distal end to be inserted percutaneously into an accessible blood vessel, shown in FIG. 1 as the right femoral vein. The supply catheter 12 is sufficiently long to allow the heat transfer element 14 at the distal end of the supply catheter 12 to be passed through the vascular system of the patient and placed in the blood vessel of interest, here the inferior vena cava. The method of inserting the catheter into the patient and routing the heat transfer element 14 into a selected artery or vein is well known in the art.

In the embodiment of FIG. 1, the narrowest blood vessel encountered by the heat transfer element as it travels to the inferior vena cava is the femoral artery, which generally ranges from 5 to 8 mm in diameter. Accordingly, in this embodiment of the invention, the diameter of the heat transfer element is about 4 to 5 mm in diameter.

In order to obtain the benefits associated with hypothermia during a coronary bypass procedure, it is desirable to reduce the temperature of the blood flowing within the body to less than 35° C., more preferably between 30 and 35° C., and most preferably 32±2° C. Given a typical blood flow rate of approximately 2.5 to 4 l/min, more typically about 3.5 l/min, in the inferior vena cava, the heat transfer element preferably absorbs 200 to 300 Watts of heat when placed in this vein, in order to induce the desired cooling effect. Approximate cooling time is 15 to 30 minutes.

Cooling the body to less than 35° C. provides a number of desirable effects. First, cooling will induce a bradycardia of the heart. Reduced heart rates corresponding to about ⅔ of the normal heart rate are common at the preferred temperature of 32±2° C. By slowing the beating of the heart, the present invention facilitates surgery during beating heart procedures. Such procedures are well known in the art. For example, the performance of coronary surgery on the beating heart is described by Benetti et al in "Coronary Revascularization With Arterial Conduits Via a Small Thoracotomy and Assisted by Thoracoscopy, Although Without Cardiopulmonary Bypass", Cor. Europatum, 4(1): 22-24 (1995), and by Westaby, "Coronary Surgery Without Cardiopulmonary Bypass" in the March, 1995 issue of the British Heart Journal. Additional discussion of this subject matter can be found in Benetti et al, "Direct myocardial revascularization without extracorporeal circulation. Experience in 700 patients", Chest, 100(2): 312-16 (1991), Pfister et al, "Coronary artery bypass without cardiopulmonary bypass" Ann. Thorac. Surg., 54:1085-92 (1992), and Fanning et al, "Reoperative coronary artery bypass grafting without cardiopulmonary bypass", Ann. Thorac. Surg., 55:486-89 (1993). Each of the above articles is hereby incorporated by reference.

Moreover, the general anesthesia associated with coronary bypass techniques is often accompanied by vasodilation in the patient, which decreases organ perfusion and hence increases the risk of ischemia. This effect, however, is combated by the hypothermia induced in accordance with the present invention, which promotes vasoconstriction.

Cooling the body also protects the organs from ischemic damage due to low circulatory flow rates or due to emboli formation. For example, as previously noted, procedures are known in the art in which (1) the heart is intermittently stopped and restarted or (2) the heart is stopped and a small intracorporeal pump is used to provide circulatory support. These techniques and others like them allow the surgeon to operate on a still or nearly still heart. However, each of these techniques also places the patient at risk from ischemia. By lowering the body temperature of the patient to a preferred temperature of 32±2° C. in accordance with the present invention, however, the oxygen demand of the bodily tissue, and hence the danger of ischemia associated with these procedures, is reduced.

More specifically, with some techniques in which alternating periods of heartbeat and heart arrest are provided, the heart is stopped or nearly stopped using drugs such as beta-blockers, and a pacing device is used to cause the heart to beat on demand. An example of one such system is the TRANSARREST system; Corvascular, Inc., Palo Alto, Calif. In other techniques, the heart is momentarily stopped or slowed by electrically stimulating the vagus nerve. See, e.g., U.S. Pat. Nos. 5,913,876 and 6,006,134, the disclosures of which are hereby incorporated by reference. (As noted in U.S. Pat. No. 5,913,876, one or more heart pacing devices, such as a Pace port-Swann pulmonary artery catheter, may be inserted in conventional fashion to the patient's heart and used to restore the beating of the heart during the surgery, in the event the heart is slow to revive after a nerve stimulating signal is turned off.) Each of these techniques is associated with a circulatory flow rate that can be significantly lower than normal cardiac output.

The risks of ischemia due to low circulatory flow rates, however, are reduced in accordance with an embodiment of the invention. In particular, before manipulating the heartbeat of the patient, a heat transfer element is inserted into the vasculature of the patient and the body temperature of the patient is reduced, preferably to 32±2° C. As noted above, by lowering the body temperature, the body's oxygen demand is reduced, decreasing the risk of ischemia. Moreover, a reduction in body temperature in accordance with the present invention is accompanied by vasoconstriction, which decreases the circulatory flow rate that is required for adequate organ perfusion and consequently further decreases the risk of ischemia.

The present invention is also useful in connection with techniques in which the heart is stopped or nearly stopped and an intracorporeal pump is used to support circulation. For example, techniques are known in which circulatory support is provided during coronary bypass by a pump positioned in the patient's aortic valve. See, for example, M. S. Sweeney, "The Hemopump in 1997: A Clinical, Political, and Marketing Evolution", Ann. Thorac. Surg., 1999, Vol. 68, pp. 761-3, the entire disclosure of which is hereby incorporated by reference. In this reference, a coronary bypass operation is described in which esmolol, a short acting beta-blocker, is administered to calm the heart during surgery. A Medtronic Hemopump® is used for circulatory support and the patient's own lungs are used for oxygenation. At the core of the Hemopump is a small, rapidly turning Archimedes screw. The pump assembly is made of stainless steel and is attached to a silicone rubber inlet cannula. The cannula is positioned across the aortic valve and into the left ventricle. The pump assembly is catheter mounted to facilitate placement of the pump in its operating position. For example, the pump assembly is ordinarily inserted into the femoral artery of the thigh, whereupon it is guided to the left ventricle. Once in place, the cannula acts to entrain blood and feeds it to the pump portion, which then pumps the blood into circulation via the aorta. The pump is operated by the creation of pulsing electromagnetic fields, which cause rotation of a permanent magnet, resulting in operation of the Archimedes screw. Electrical power is provided from a console outside the patient. The pumping action is axial and continuous (i.e., non-pulsatile). Due to the design of the Hemopump, rotational speeds on the order of 10,000 to 20,000 rpm can be used to produce blood flow of about four liters per minute or less (depending on the model) without significant hemolysis. Additional details are found in M. C. Sweeney and O. H. Frazier, "Device-supported myocardial revascularization; safe help for sick hearts", Ann. Thorac. Surg. 1992, 54: 1065-70 and U.S. Pat. No. 4,625,712, the entire disclosures of which are hereby incorporated by reference.

This technique and others like it, however, are frequently associated with circulatory flow rates (i.e., about 4 l/min or less) that are lower than normal cardiac output (i.e., about 5 l/min for many people) placing the patient at ischemic risk. By lowering the body temperature of the patient to a preferred range of 32±2° C. in accordance with the present invention, however, the blood vessels are constricted and oxygen demand of the bodily tissue is reduced, increasing organ perfusion and reducing the danger of ischemia for a given circulatory output.

As noted above, in a preferred embodiment of this first aspect of the invention, the heat transfer element is provided in the inferior vena cava, which is accessed via the femoral vein. In contrast, the Hemopump is preferably provided in the left ventricle, which is accessed via the femoral artery. In this way, both the heating element and the Hemopump can be concurrently placed in the body in a minimally invasive fashion.

According to another aspect of the invention, a hypothermic medical procedure is performed on a patient in a conscious or semiconscious state. An example of a situation where such a hypothermic medical procedure may be performed is one in which a patient has suffered a stroke and hypothermia is induced in the brain to reduce ischemic damage.

Such procedures can be performed either to cool the entire body of the patient or a region within the patient's body, typically an organ.

The entire body can be cooled using the procedures discussed above. For example, the heat transfer element is preferably provided in a venous blood vessel, more preferably the inferior vena cava, to effect cooling of the entire body.

In order to intravascularly regulate the temperature of a selected region, the heat transfer element may be placed in a feeding artery of the region to absorb or deliver the heat from or to the blood flowing into the region. The heat transfer element should be small enough to fit within the feeding artery while still allowing a sufficient blood flow to reach the region in order to avoid ischemic damage. By placing the heat transfer element within the feeding artery of a region, the temperature of the region can be controlled, while having less effect on the remaining parts of the body. Using the brain as an example, the common carotid artery supplies blood to the head and brain. The internal carotid artery branches off of the common carotid to directly supply blood to the brain. To selectively cool the brain, the heat transfer element is placed into the common carotid artery, or both the common carotid artery and the internal carotid artery. The internal diameter of the common carotid artery ranges from 6 to 8 mm and the length ranges from 80 to 120 mm. Thus, the heat transfer element residing in one of these arteries cannot be much larger than 4 mm in diameter in order to avoid occluding the vessel, which would result, for example, in ischemic damage.

When hypothermia is induced in a patient, less than desirable side effects can occur in the patient. For example, hypothermia is known to activate the sympathetic nervous system in a conscious or semiconscious patient, resulting in a significant norepinephrine response. Norepinephrine, in turn, binds to beta sites including those in the heart, causing the heart to beat harder and more rapidly, frequently resulting in cardiac arrythmia and increased risk of myocardial ischemia. In accordance with an embodiment of the present invention, however, a beta-blocker is administered to the patient. Without wishing to be bound by theory, it is believed that the beta-blocker offsets the norepinephrine binding noted above. In general, the beta-blocker may be administered before the patient cooling commences, and preferably immediately before patient cooling commences.

Preferred beta-blockers for this aspect of the invention include β1 blockers, β1β2 blockers and αβ1β2 blockers. Preferred β1 blockers include acebutolol, atenolol, betaxolol, bisoprolol, esmolol and metoprolol. Preferred β1β2 blockers include carteolol, nadolol, penbutolol, pindolol, propranolol, sotalol and timolol. Preferred αβ1β2 blockers include carvedilol and labetalol.

The heightened demand that hypothermia places on the heart of conscious or semiconscious patents may also be relieved, for example, with heating blankets. However, vasoconstriction limits the heating ability of the heating blankets. Without wishing to be bound by theory, it is believed that the above-noted production of norepinephrine activates alpha-receptors, for example, in the peripheral blood vessels, causing this vasoconstriction. The vasoconstriction can be offset, in accordance with the present invention, by treating the patient with alpha-blockers when indicated, preferably before cooling is initiated. Preferred alpha-blockers include labetalol and carvedilol.

In the various embodiments of the invention, once the medical procedure is completed, the heat transfer element is preferably used to warm the body back to its normal temperature, i.e., 37° C.

Regarding the construction of the heat transfer element, this component is ideally a flexible element, allowing it to be placed at the desired vascular position. For example, the element often has to be passed though a series of one or more venous or arterial branches, making flexibility an important characteristic of the heat transfer element.

Further, the heat transfer element is ideally constructed from a highly thermally conductive material such as metal or very thin plastics or polymers, in order to facilitate heat transfer. The use of a highly thermally conductive material increases the heat transfer rate for a given temperature differential between the fluid within the heat transfer element and the blood. Highly thermally conductive materials, such as metals, tend to be rigid. Therefore, the design of the heat transfer element should facilitate flexibility in an inherently inflexible material.

In general, the magnitude of the heat transfer rate is proportional to the surface area of the heat transfer element, the temperature differential, and the heat transfer coefficient of the heat transfer element.

Diameter, and hence surface area, of the heat transfer element is limited to avoid significant obstruction of the vein or artery and to allow the heat transfer element to easily pass through the vascular system. As noted above, for placement within the inferior vena cava, the cross sectional diameter of the heat transfer element is about 4-5 mm. For placement in the internal carotid artery, the cross sectional diameter is about 2 to 3.5 mm. Typically, the length of the heat transfer element for this purpose is about 10 to 30 cm.

When used in cooling mode, decreasing the surface temperature of the heat transfer element can increase the temperature differential. However, the minimum allowable surface temperature is limited by the characteristics of blood. Blood freezes at approximately 0° C. When the blood approaches freezing, ice emboli may form in the blood that may lodge downstream, causing serious ischemic injury. Furthermore, reducing the temperature of the blood also increases its viscosity, which results in a small decrease in the value of the convection heat transfer coefficient. In addition, increased viscosity of the blood may result in an increase in the pressure drop within the artery or vein, thus compromising the flow of blood to the organs. Given the above constraints, it is advantageous to limit the minimum allowable surface temperature of the heat transfer element to approximately 5° C. This results in a maximum temperature differential between the blood stream and the heat transfer element of approximately 32° C. when the heat transfer device is used in cooling mode.

Similarly, when in heating mode, increasing the surface temperature of the heat transfer element can increase the temperature differential. Analogous to cooling, however, the maximum allowable surface temperature is limited by the characteristics of blood. In particular, damage to blood components can occur at temperatures of about 45-48° C. and above. Accordingly, it is advantageous to limit the maximum allowable surface temperature of the heat transfer element to approximately 44° C. This results in a maximum temperature differential between the blood stream and the heat transfer element of approximately 7° C. when the heat transfer device is used in heating mode.

The mechanisms by which the value of the convection heat transfer coefficient may be increased are complex. However, it is well known that the convection heat transfer coefficient increases with the level of turbulent kinetic energy in the fluid flow. Thus it is advantageous to have turbulent or mixing blood flow in contact with the heat transfer element.

Specifically, creating a turbulent boundary layer on the heat transfer element surface can increase the heat transfer rate. In the event that a smooth heat transfer element is used, turbulence normally occurs in a very thin boundary layer, producing only a small amount of turbulent kinetic energy and resulting in less than optimal heat transfer. Therefore, to induce increase turbulent kinetic energy (and thus to increase the heat transfer rate), a stirring mechanism that abruptly changes the direction of velocity vectors is preferably utilized. This can create high levels of turbulence intensity in the free stream (and not just the boundary layer), thereby sufficiently increasing the heat transfer rate. If the flow of blood is continuous (non-pulsatile) flow (such as encountered in venous flow), this turbulence or mixing intensity should be maintained at all times. In the event that blood flow is pulsatile flow (such as is encountered in arterial flow), the mixing intensity should be maintained over a majority of the pulsatile period (e.g., the cardiac cycle).

Figure 2:
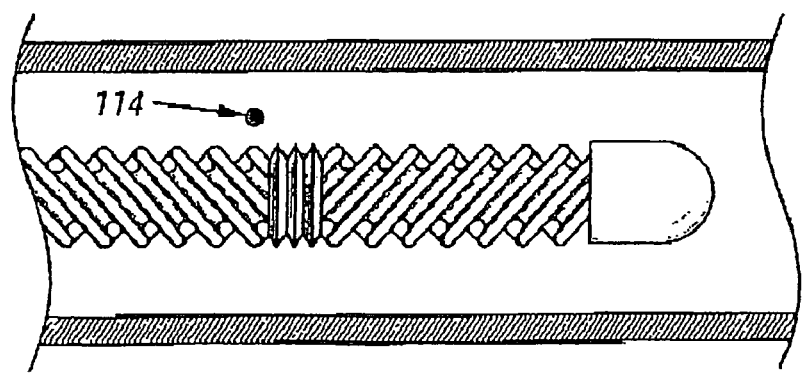
FIG. 2 is an elevation view of a mixing inducing heat transfer element within a blood vessel in accordance with an embodiment of the invention.

To create the desired level of mixing intensity in the blood free stream, in one preferred embodiment, the heat transfer element is provided with a modular design. This design creates helical blood flow and produces a high level of mixing in the free stream by periodically forcing abrupt changes in the direction of the helical blood flow. FIG. 2 is a perspective view of such a mixing inducing heat transfer element within a blood vessel. Mixed flow is indicated at point 114, in the free stream area. The abrupt changes in flow direction are achieved through the use of a series of two or more heat transfer segments, each comprised of one or more helical ridges.

The use of periodic abrupt changes in the helical direction of the blood flow in order to induce strong free stream turbulence or mixing may be illustrated with reference to a common clothes washing machine. The rotor of a washing machine spins initially in one direction causing laminar flow. When the rotor abruptly reverses direction, significant turbulent kinetic energy is created within the entire washbasin as the changing currents cause random turbulent motion within the clothes-water slurry.

FIG. 3 is an elevation view of one embodiment of a heat transfer element 14. The heat transfer element 14 is comprised of a series of elongated, articulated segments or modules 20, 22, 24. Three such segments are shown in this embodiment, but one or more such segments could be used without departing from the spirit of the invention. As seen in FIG. 3, a first elongated heat transfer segment 20 is located at the proximal end of the heat transfer element 14. A mixing-inducing exterior surface of the segment 20 comprises four parallel helical ridges 38 with four parallel helical grooves 26 therebetween. One, two, three, or more parallel helical ridges 38 could also be used. In this embodiment, the helical ridges 38 and the helical grooves 26 of the heat transfer segment 20 have a left hand twist, referred to herein as a counter-clockwise spiral or helical rotation, as they proceed toward the distal end of the heat transfer segment 20.

The first heat transfer segment 20 is coupled to a second elongated heat transfer segment 22 by a first bellows section 25, which provides flexibility and compressibility. The second heat transfer segment 22 comprises one or more helical ridges 32 with one or more helical grooves 30 therebetween. The ridges 32 and grooves 30 have a right hand, or clockwise, twist as they proceed toward the distal end of the heat transfer segment 22. The second heat transfer segment 22 is coupled to a third elongated heat transfer segment 24 by a second bellows section 27. The third heat transfer segment 24 comprises one or more helical ridges 36 with one or more helical grooves 34 therebetween. The helical ridge 36 and the helical groove 34 have a left hand, or counter-clockwise, twist as they proceed toward the distal end of the heat transfer segment 24. Thus, successive heat transfer segments 20, 22, 24 of the heat transfer element 14 alternate between having clockwise and counterclockwise helical twists. The actual left or right hand twist of any particular segment is immaterial, as long as adjacent segments have opposite helical twist.

In addition, the rounded contours of the ridges 38, 32, 36 also allow the heat transfer element 14 to maintain a relatively atraumatic profile, thereby minimizing the possibility of damage to the blood vessel wall.

The bellows sections 25,27 are formed from seamless and nonporous materials, typically metals such as nickel, copper, etc. The structure of the bellows sections 25, 27 allows them to bend, extend and compress, which increases the flexibility of the heat transfer element 14 so that it is more readily able to navigate through blood vessels. The bellows sections 25, 27 also provide for axial compression of the heat transfer element 14, which can limit the trauma when the distal end of the heat transfer element 14 abuts a blood vessel wall. The bellows sections 25, 27 are also able to tolerate cryogenic temperatures without a loss of performance.

It may be desirable to treat the surfaces of the heat transfer element 14 to avoid clot formation. In particular, one may wish to treat the bellows sections 25, 27 because stagnation of the blood flow may occur in the convolutions, thus allowing clots to form and cling to the surface to form a thrombus. One means by which to prevent thrombus formation is to bind an antithrombogenic agent to the surface of the heat transfer element 14. For example, heparin is known to inhibit clot formation and is also known to be useful as a biocoating. Alternatively, the surfaces of the heat transfer element 14 may be bombarded with ions such as nitrogen. Bombardment with nitrogen can harden and smooth the surface and thus prevent adherence of clotting factors to the surface.

FIG. 4 is a longitudinal sectional view of the heat transfer element 14 of an embodiment of the invention, taken along line 5-5 in FIG. 3. Some interior contours are omitted for purposes of clarity. An inner tube 42 creates an inner coaxial lumen 42 and an outer coaxial lumen 46 within the heat transfer element 14. Once the heat transfer element 14 is in place in the blood vessel, a working fluid such as saline or other aqueous solution may be circulated through the heat transfer element 14. Fluid flows up a supply catheter into the inner coaxial lumen 40. At the distal end of the heat transfer element 14, the working fluid exits the inner coaxial lumen 40 and enters the outer lumen 46. As the working fluid flows through the outer lumen 46, heat is transferred from the working fluid to the exterior surface 37 of the heat transfer element 14, or vice versa. Because the heat transfer element 14 is constructed from a high conductivity material, the temperature of its exterior surface 37 may reach very close to the temperature of the working fluid. The tube 42 may be formed as an insulating divider to thermally separate the inner lumen 40 from the outer lumen 46. For example, insulation may be achieved by creating longitudinal air channels in the wall of the insulating tube 42. Alternatively, the insulating tube 42 may be constructed of a non-thermally conductive material like polytetrafluoroethylene or some other polymer.

The same mechanisms that govern the heat transfer rate between the exterior surface 37 of the heat transfer element 14 and the blood also govern the heat transfer rate between the working fluid and the interior surface 38 of the heat transfer element 14. The heat transfer characteristics of the interior surface 38 are particularly important when using water, saline or other fluid that remains a liquid as the coolant. Other coolants such as Freon undergo nucleate boiling and create turbulence through a different mechanism. Saline is a safe coolant because it is non-toxic, and leakage of saline does not result in a gas embolism, which could occur with the use of boiling refrigerants. Since turbulence or mixing in the coolant is enhanced by the shape of the interior surface 38 of the heat transfer element 14, the coolant can be delivered to the heat transfer element 14 at a warmer temperature and still achieve the necessary heat transfer rate.

Further details and embodiments concerning the heat transfer element design and operation can be found in commonly assigned WO 99/48449, the complete disclosure of which is incorporated by reference.

In a further embodiment of the invention, the heat transfer element is made of a flexible material, such as latex rubber. The latex rubber provides a high degree of flexibility which was previously achieved by articulation. The latex rubber further allows the heat transfer element to be made collapsible so that when deflated the same may be easily inserted into an artery. Insertion and location may be conveniently made by way of a guide catheter or guide wire. Following insertion and location in the desired artery, the heat transfer element may be inflated for use by a working fluid such as saline, water, perfluorocarbons, or other suitable fluids.

A heat transfer element made of a flexible material generally has significantly less thermal conductivity than a heat transfer element made of metal. The device compensates for this by enhancing the surface area available for heat transfer. This may be accomplished in two ways: by increasing the cross-sectional size and by increasing the length. Regarding the former, the device may be structured to be large when inflated, because when deflated the same may still be inserted into an artery. In fact, the device may be as large as the arterial wall, so long as a path for blood flow is allowed, because the flexibility of the device tends to prevent damage to the arterial wall even upon contact. Such paths are described below. Regarding the latter, the device may be configured to be long. One way to configure a long device is to taper the same so that the device may fit into distal arteries having reduced radii in a manner described below. The device further compensates for the reduced thermal conductivity by reducing the thickness of the heat transfer element wall.

Embodiments of the device use a heat transfer element design that produces a high level of turbulence in the free stream of the blood and in the working fluid. One embodiment of the invention forces a helical motion on the working fluid and imposes a helical barrier in the blood, causing turbulence. In an alternative embodiment, the helical barrier is tapered. In a second alternative embodiment, a tapered inflatable heat transfer element has surface features to cause turbulence. As one example, the surface features may have a spiral shape. In another example, the surface features may be staggered protrusions. In all of these embodiments, the design forces a high level of turbulence in the free stream of the blood by causing the blood to navigate a tortuous path while passing through the artery. This tortuous path causes the blood to undergo violent accelerations resulting in turbulence.

In a third alternative embodiment of the invention, a taper of an inflatable heat transfer element provides enough additional surface area per se to cause sufficient heat transfer. In all of the embodiments, the inflation is performed by the working fluid, such as water or saline.

Figure 5:
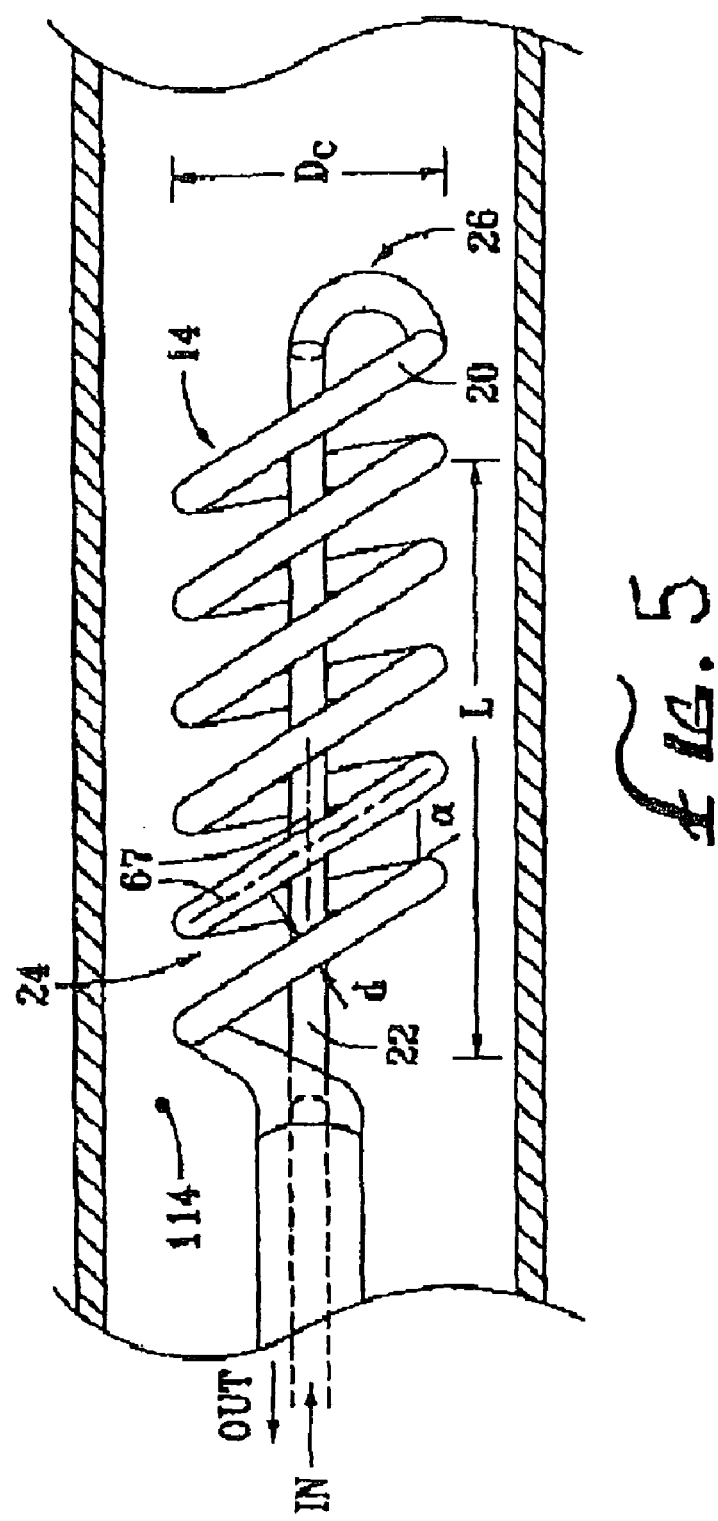
FIG. 5 is a side schematic view of an inflatable turbulence-inducing heat transfer element according to an embodiment of the invention, as the same is disposed within an artery.

Referring to FIG. 5, a side view is shown of a first embodiment of a heat transfer element 14 according to an embodiment of the invention. The heat transfer element 14 is formed by an inlet lumen 22 and an outlet lumen 20. In this embodiment, the outlet lumen 20 is formed in a helix shape surrounding the inlet lumen 22 that is formed in a pipe shape. The names of the lumens are of course not limiting. It will be clear to one skilled in the art that the inlet lumen 22 may serve as an outlet and the outlet lumen 20 may serve as an inlet. It will also be clear that the heat transfer element is capable of both heating (by delivering heat to) and cooling (by removing heat from) a desired area.

The heat transfer element 14 is rigid but flexible so as to be insertable in an appropriate vessel by use of a guide catheter. Alternatively, the heat transfer element may employ a device for threading a guide wire therethrough to assist placement within an artery. The heat transfer element 14 has an inflated length of L, a helical diameter of $D_c$, a tubal diameter of d, and a helical angle of $\alpha$. For example, $D_c$ may be about 3.3 mm and d may be about 0.9 mm to 1 mm. Of course, the tubal diameter d need not be constant. For example, the diameter of the inlet lumen 22 may differ from that of the outlet lumen 20.

The shape of the outlet lumen 20 in FIG. 5 is helical. This helical shape presents a cylindrical obstacle, in cross-section, to the flow of blood. Such obstacles tend to create turbulence in the free stream of blood. In particular, the form of turbulence is the creation of von Karman vortices in the wake of the flow of blood, downstream of the cylindrical obstacles.

Typical inflatable materials are not highly thermally conductive. They are much less conductive than the metallic heat transfer element disclosed in the patent application incorporated by reference above. The difference in conductivity is compensated for in at least two ways in the present device. The material is made thinner and the heat transfer element is afforded a larger surface area. Regarding the former, the thickness may be less than about ½ mil for adequate cooling.

Thin inflatable materials, particularly those with large surface areas, may require a structure, such as a wire, within their interiors to maintain their approximate uninflated positions so that upon inflation, the proper form is achieved. Thus, a wire structure 67 is shown in FIG. 5 which may be advantageously disposed within the inflatable material to perform such a function.

Another consideration is the angle $\alpha$ of the helix. Angle $\alpha$ should be determined to optimize the helical motion of the blood around the lumens 20 and 22, enhancing heat transfer. Of course, angle $\alpha$ should also be determined to optimize the helical motion of the working fluid within the lumens 20 and 22. The helical motion of the working fluid within the lumens 20 and 22 increases the turbulence in the working fluid by creating secondary motions. In particular, helical motion of a fluid in a pipe induces two counter-rotating secondary flows.

An enhancement of $h_c$ would be obtained in this system, and this enhancement may be described by a Nusselt number Nu of up to about 10 or even more.

Figure 6:
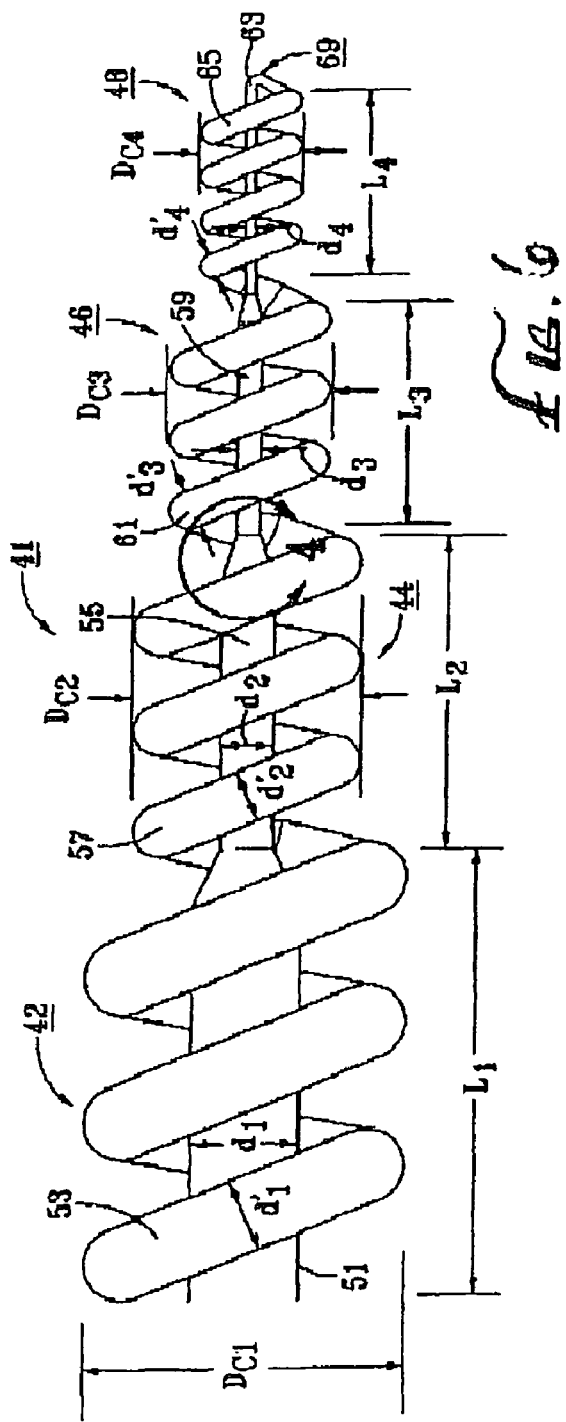
FIG. 6 illustrates an inflatable turbulence-inducing heat transfer element according to an alternative embodiment of the invention employing a surface area enhancing taper and a turbulence-inducing shape.

The above discussion describes one embodiment of a heat transfer element. An alternative embodiment of the device, shown in a side view in FIG. 6, illustrates a heat transfer element 41 with a surface area enhancement. Increasing the surface area of the inflatable material enhances heat transfer. The heat transfer element 14 includes a series of coils or helices of different coil diameters and tubal diameters. It is not strictly necessary that the tubal diameters differ, but it is likely that commercially realizable systems will have differing tubal diameters. The heat transfer element 14 may taper either continuously or segmentally.

This alternative embodiment enhances surface area in two ways. First, the use of smaller diameter lumens enhances the overall surface-to-volume ratio. Second, the use of progressively smaller (i.e., tapered) lumens allows a distal end 69 to be inserted further into an artery than would be possible with the embodiment of FIG. 5.

In the embodiment of FIG. 6, a first coil segment 42 is shown having length $L_1$ and diameter $D_{C1}$. The first coil segment 42 is formed of an inlet lumen 51 having diameter $d_1$ and an outlet lumen 53 having diameter $d_{1'}$. In the first coil segment, as well as the others, the outlet lumen need not immediately drain the inlet lumen. In FIG. 6, the inlet lumen for each segment feeds the inlet lumen of the succeeding segment except for an inlet lumen adjacent a distal end 69 of the heat transfer element 41 which directly feeds its corresponding outlet lumen.

A separate embodiment may also be constructed in which the inlet lumens each provide working fluid to their corresponding outlet lumens. In this embodiment, either a separate lumen needs to be provided to drain each outlet lumen or each outlet lumen rains into the adjacent outlet lumen. This embodiment has the advantage that an opposite helicity may be accorded each successive segment. The opposite helicities in turn enhance the turbulence of the working fluid flowing past them. A second coil segment 44 is shown having length $L_2$ and diameter $D_{c2}$. The second coil segment 44 is formed of an inlet lumen 55 having diameter $d_2$ and an outlet lumen 57 having diameter $d_{2'}$. A third coil segment 46 is shown having length $L_3$ and diameter $D_{C3}$. The third coil segment 46 is formed of an inlet lumen 59 having diameter $d_3$ and an outlet lumen 61 having diameter $d_{3'}$. Likewise, a fourth coil segment 48 is shown having length $L_4$ and diameter $D_{C4}$. The fourth coil segment 48 is formed of an inlet lumen 63 having diameter $d_4$ and an outlet lumen 65 having diameter $d_{4'}$. The diameters of the lumens, especially that of the lumen located at or near distal end 69, should be large enough to not restrict the flow of the working fluid within them. Of course, any number of lumens may be provided depending on the requirements of the user.

Figure 7:
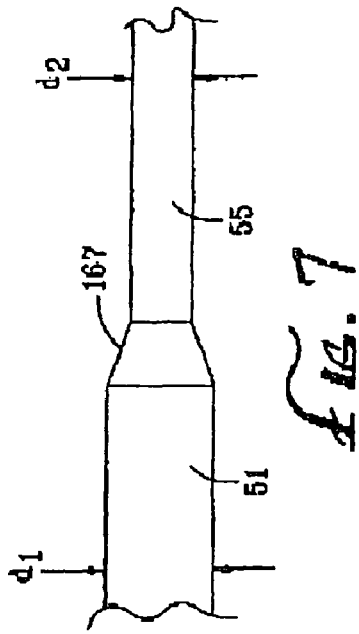
FIG. 7 illustrates a tapered joint which may be employed in the embodiment of FIG. 6.

FIG. 7 shows the connection between two adjacent inlet lumens 51 and 55. A joint 167 is shown coupling the two lumens. The construction of the joint may be by way of variations in stress, hardening, etc.

An advantage to this alternative embodiment arises from the smaller diameters of the distal segments. The heat transfer element of FIG. 6 may be placed in smaller workspaces than the heat transfer element of FIG. 5. For example, a treatment for brain trauma may include placement of a cooling device in the internal carotid artery of a patient. As noted above, the common carotid artery feeds the internal carotid artery. In some patients, the heat transfer element of FIG. 5 may not fit in the internal carotid artery. Similarly, the first coil segment of the heat transfer element in FIG. 6 may not easily fit in the internal carotid artery, although the second, third, and fourth segments may fit. Thus, in the embodiment of FIG. 6, the first coil segment may remain in the common carotid artery while the segments of smaller diameter (the second, third, and fourth) may be placed in the internal carotid artery. In fact, in this embodiment, $D_{c1}$, may be large, such as 5-6 mm. The overall length of the heat transfer element 41 may be, e.g., about 20 to 25 cm.

An additional advantage was mentioned above. The surface area of the alternative embodiment of FIG. 6 may be substantially larger than that of the embodiment of FIG. 5, resulting in significantly enhanced heat transfer. For example, the enhancement in surface area may be substantial, such as up to or even more than three times compared to the surface area of the device of the application incorporated by reference above. An additional advantage of both embodiments is that the helical rounded shape allows a traumatic insertion into cylindrical cavities such as, e.g., arteries.

The embodiment of FIG. 6 may result in an Nu from 1 up to about 50.

FIG. 8 shows a second alternative embodiment of the device employing surface features rather than overall shape to induce turbulence. In particular, FIG. 8 shows a heat transfer element 201 having an inlet lumen (not shown) and an outlet inflatable lumen 220 having four segments 203, 205, 207, and 221. Segment 203 is adjacent a proximal end 211 and segment 221 is adjacent a distal end 213. The segments are arranged having reducing radii in the direction of the proximal end to the distal end. In a manner similar to that of the embodiment of FIG. 6, the feature of reducing radii allows insertion of the heat transfer element into small work places such as small arteries.

Heat transfer element 201 has a number of surface features 215 disposed thereon. The surface features 215 may be constructed with, e.g., various hardening treatments applied to the heat transfer element 201, or alternatively by injection molding. The hardening treatments may result in a wavy or corrugated surface to the exterior of heat transfer element 201. The hardening treatments may further result in a wavy or corrugated surface to the interior of heat transfer element 201. FIG. 9 shows a variation of this embodiment, in which a fabrication process is used which results in a spiral or helical shape to the surface features.

The embodiment of FIG. 8 may result in an Nu of about 1 to 50.

In another variation of this embodiment, shown in FIG. 10, a heat transfer element 150 employs a plurality of protrusions 154 on outlet lumen 152 which surrounds an inlet lumen 158. In particular, FIG. 10 is a cut-away perspective view of an alternative embodiment of a heat transfer element 150. A working fluid is circulated through an inlet lumen 156 to a distal tip of the heat transfer element 150 thereby inflating the heat transfer element 150. The working fluid then traverses an outlet coaxial lumen 160 in order to transfer heat from the exterior surface 152 of the heat transfer element 150. The inside structure of the heat transfer element 150 is similar to the exterior structure in order to induce turbulent flow of the working fluid.

An external surface 152 of the inflatable heat transfer element 150 is covered with a series of staggered protrusions 154. The staggered nature of the protrusions 154 is readily seen with reference to FIG. 11 which is a transverse cross-sectional view of an inflated heat transfer element taken along the line 8-8 in FIG. 10. In order to induce free stream turbulence, the height, $d_p$, of the staggered protrusions 154 is greater than the thickness of the boundary layer which would develop if a smooth heat transfer element had been introduced into the blood stream. As the blood flows along the external surface 152, it collides with one of the staggered protrusions 154 and a turbulent flow is created. As the blood divides and swirls along side of the first staggered protrusion 154, it collides with another staggered protrusion 154 within its path preventing the re-lamination of the flow and creating yet more turbulence. In this way, the velocity vectors are randomized and free stream turbulence is created. As is the case with the other embodiments, this geometry also induces a turbulent effect on the internal coolant flow.

The embodiment of FIG. 10 may result in an Nu of about 1 to 50.

Of course, other surface features may also be used which result in turbulence in fluids flowing past them. These include spirals, helices, protrusions, various polygonal bodies, pyramids, tetrahedrons, wedges, etc.

In some situations, an enhanced surface area alone, without the creation of additional turbulence, may result in sufficient heat transfer to cool the blood. Referring to FIG. 12, a heat transfer element 302 is shown having an inlet lumen 304 and an outlet lumen 306. The inlet lumen 304 provides a working fluid to the heat transfer element 302 and outlet lumen 306 drains the working fluid from the same. The functions may, of course, be reversed. The heat transfer element 302 is further divided into five segments, although more or less may be provided as dictated by requirements of the user. The five segments in FIG. 12 are denoted segments 308, 310, 312, 314, and 316. In FIG. 12, the segment 308 has a first and largest radius $R_1$, followed by corresponding radii for segments 310, 312, 314, and 316. Segment 316 has a second and smallest radius. The length of the segment 308 is $L_1$, followed by corresponding lengths for segments 310, 312, 314, and 316.

A purely tapered (nonsegmented) form may replace the tapered segmental form, but the former may be more difficult to manufacture. In either case, the tapered form allows the heat transfer element 302 to be disposed in small arteries, i.e., arteries with radii smaller than $R_1$. A sufficient surface area is thus afforded even in very small arteries to provide the required heat transfer.

The surface area and thus the size of the device should be substantial to provide the necessary heat transfer. Example dimensions for a three-segmented tapered form may be as follows: $L_1$=10 cm, $R_1$=2.5 mm; $L_2$=10 cm, $R_2$=1.65 mm, $L_3$=5 cm, $R_3$=1 mm. Such a heat transfer element would have an overall length of 25 cm and a surface area of $3 \times 10^{-4}$ m.

The embodiment of FIG. 12 results in an enhancement of the heat transfer rate of up to about 300% due to the increased surface area S alone.

A variation of the embodiment of FIG. 12 includes placing at least one turbulence-inducing surface feature within the interior of the outlet lumen 306. This surface feature may induce turbulence in the working fluid, thereby increasing the convective heat transfer rate in the manner described above.

Another variation of the embodiment of FIG. 12 involves reducing the joint diameter between segments (not shown). For example, the inflatable material may be formed such that joints 318, 320, 322, and 324 have a diameter only slightly greater than that of the inlet lumen 304. In other words, the heat transfer element 302 has a tapered "sausage" shape.

In all of the embodiments, the inflatable material may be formed from seamless and nonporous materials which are therefore impermeable to gas. Impermeability can be particularly important depending on the type of working fluid which is cycled through the heat transfer element. For example, the inflatable material may be latex or other such rubber materials, or alternatively of any other material with similar properties under inflation. The flexible material allows the heat transfer element to bend, extend and compress so that it is more readily able to navigate through tiny blood vessels. The material also provides for axial compression of the heat transfer element which can limit the trauma when the distal end of the heat transfer element 14 abuts a blood vessel wall. The material should be chosen to tolerate temperatures in the range of −1° C. to 37° C., or even higher in the case of blood heating, without a loss of performance.

It may be desirable to treat the surface of the heat transfer element to avoid clot formation because the heat transfer element may dwell within the blood vessel for extended periods of time, such as 24-48 hours or even longer. One means by which to prevent thrombus formation is to bind an antithrombogenic agent to the surface of the heat transfer element. For example, heparin is known to inhibit clot formation and is also known to be useful as a biocoating.

Referring back to FIG. 5, an embodiment of the method of the invention will be described. A description with reference to the embodiment of FIG. 6 is analogous. A guide catheter or wire may be disposed up to or near the area to be cooled or heated. The case of a guide catheter will be discussed here. The heat transfer element may be fed through the guide catheter to the area. Alternatively, the heat transfer element may form a portion of the guide catheter. A portion of the interior of the guide catheter may form, e.g., the return lumen for the working fluid. In any case, the movement of the heat transfer element is made significantly more convenient by the flexibility of the heat transfer element as has been described above.

Once the heat transfer element 14 is in place, a working fluid such as saline or other aqueous solution may be circulated through the heat transfer element 14 to inflate the same. Fluid flows from a supply catheter into the inlet lumen 22. At the distal end 26 of the heat transfer element 14 the working fluid exits the inlet lumen 22 and enters the outlet lumen 20.

In the case of the embodiment of FIG. 8, for which the description of FIG. 10 is analogous, the working fluid exits the inlet lumen and enters an outlet inflatable lumen 220 having segments 203, 205, 207, and 221. As the working fluid flows through the outlet lumen 220, heat is transferred from the exterior surface of the heat transfer element 201 to the working fluid. The temperature of the external surface may reach very close to the temperature of the working fluid because the heat transfer element 201 is constructed from very thin material.

The working fluids that may be employed in the device include water, saline or other fluids which remain liquid at the temperatures used. Other coolants, such as freon, undergo nucleated boiling and may create turbulence through a different mechanism. Saline is a safe coolant because it is non-toxic and leakage of saline does not result in a gas embolism which may occur with the use of boiling refrigerants.

By enhancing turbulence in the coolant, the coolant can be delivered to the heat transfer element at a warmer temperature and still achieve the necessary heat transfer rate. In particular, the enhanced heat transfer characteristics of the internal structure allow the working fluid to be delivered to the heat transfer element at lower flow rates and lower pressures. This is advantageous because high pressures may stiffen the heat transfer element and cause the same to push against the wall of the vessel, thereby shielding part of the heat transfer unit from the blood. Such pressures are unlikely to damage the walls of the vessel because of the increased flexibility of the inflated device. The increased heat transfer characteristics allow the pressure of the working fluid to be delivered at pressures as low as 5 atmospheres, 3 atmospheres, 2 atmospheres or even less than 1 atmosphere.

In a preferred embodiment, the heat transfer element creates a turbulence intensity greater than 0.05 in order to create the desired level of turbulence in the entire blood stream during the whole cardiac cycle. The turbulence intensity may be greater than 0.055, 0.06, 0.07 or up to 0.10 or 0.20 or even greater.

Figure 13:
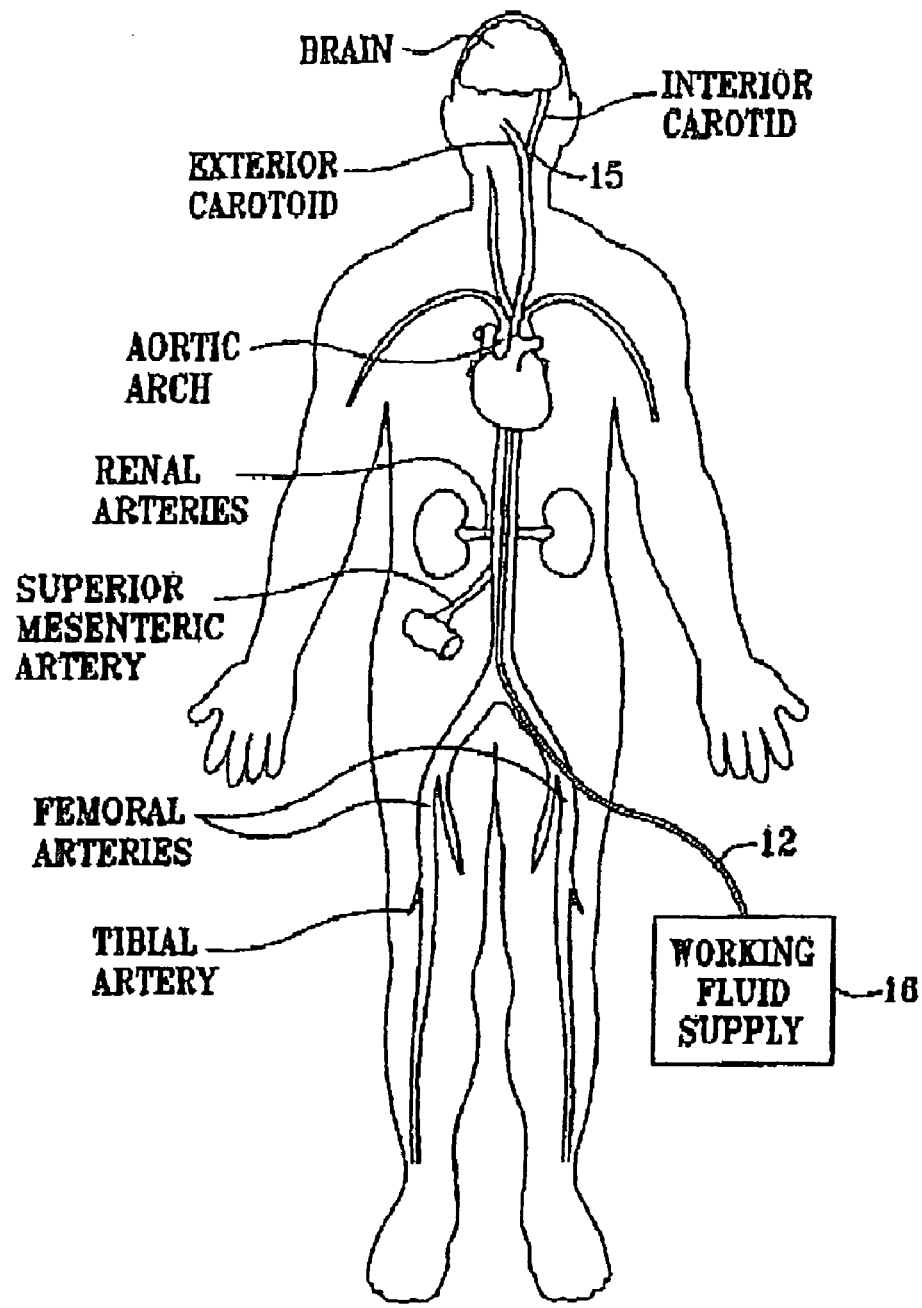
FIG. 13 is a schematic representation of an embodiment of the invention being used to cool the brain of a patient.

FIG. 13 is a schematic representation of the device being used to cool the brain of a patient. The selective organ hypothermia apparatus includes a working fluid supply 16, preferably supplying a chilled liquid such as water, alcohol or a halogenated hydrocarbon, a supply catheter 12 and the heat transfer element 15. The heat transfer element 15 may have the form, e.g., of any of the embodiments above or of similar such heat transfer elements. The supply catheter 12 has a coaxial construction. An inlet lumen within the supply catheter 12 receives coolant from the working fluid supply 16. The coolant travels the length of the supply catheter 12 to the heat transfer element 15 which serves as the cooling tip of the catheter. At the distal end of the heat transfer element 15, the coolant exits the insulated interior lumen and traverses the length of the heat transfer element 15 in order to decrease the temperature of the heat transfer element 15. The coolant then traverses an outlet lumen of the supply catheter 12, which may have a helical or other shape as described above. The supply catheter 12 is a flexible catheter having a diameter sufficiently small to allow its distal end to be inserted percutaneously into an accessible artery such as the femoral artery of a patient. The supply catheter 12 is sufficiently long to allow the heat transfer element 15 to be passed through the vascular system of the patient and placed in the internal carotid artery or other small artery. If the heat transfer element 15 employs tapering as in some of the embodiments described above, the same may be placed in very small arteries without damage to the arterial walls.

The heat transfer element can absorb or provide over 75 watts of heat to the blood stream and may absorb or provide as much as 100 watts, 150 watts, 170 watts or more. For example, a heat transfer element with a diameter of 4 mm and a length of approximately 10 cm, using ordinary saline solution chilled so that the surface temperature of the heat transfer element is approximately 5° C. and pressurized at 2 atmospheres, can absorb about 150 watts of energy from the bloodstream. Smaller geometry heat transfer elements may be developed for use with smaller organs which provide 60 watts, 50 watts, 25 watts or less of heat transfer.

Although the present invention has been described with respect to several exemplary embodiments, there are many other variations of the above-described embodiments that will be apparent to those skilled in the art. It is understood that these variations are within the teaching of the present invention, which is to be limited only by the claims appended hereto.

What is claimed is:

1. A hypothermic medical procedure comprising:
    administering a beta-blocking drug to a patient;
        delivering a heat transfer element to a blood vessel of the patient, wherein the heat transfer element comprises:
        an inlet lumen to introduce a circulating working fluid; and
        an outlet lumen to extract a circulating working fluid, the outlet lumen having a helical shape to induce turbulence in blood flowing past the outlet lumen and in the working fluid; and
    cooling a region of the patient or the body of the patient to less than 35.degree. C. using said heat transfer element while said patient is in a conscious or semiconscious state.

2. The procedure of claim 1, wherein the beta-blocking drug is a β1 blocker.

3. The procedure of claim 2, wherein the β1 blocker is selected from one or more of acebutolol, atenolol, betaxolol, bisoprolol, esmolol and metoprolol.

4. The procedure of claim 1, wherein the beta-blocking drug is a β1β2 blocker.

5. The procedure of claim 4, wherein the β1β2 blocker is selected from one or more of carteolol, nadolol, penbutolol, pindolol, propranolol, sotalol and timolol.

6. The procedure of claim 4, wherein the αβ1β2 blocker is selected from one or more of carvedilol and labetalol.

7. The procedure of claim 1, wherein the beta-blocking drug is an αβ1β2 blocker.

8. The procedure of claim 1, wherein the beta-blocking drug is administered after delivering the heat transfer element.

9. The procedure of claim 1, wherein the body of the patient is cooled.

10. The procedure of claim 1, wherein an organ of the patient is cooled.

* * * * *